(12) United States Patent
Nosil

(10) Patent No.: US 9,936,935 B1
(45) Date of Patent: Apr. 10, 2018

(54) PHANTOM SYSTEMS AND METHODS FOR DIAGNOSTIC RADIOGRAPHIC AND FLUOROSCOPIC X-RAY EQUIPMENT

(71) Applicant: Nosil DSC Innovations, Inc., Langley (CA)

(72) Inventor: Josip Nosil, Langley (CA)

(73) Assignee: Nosil DSC Innovations, Inc. (CA)

( * ) Notice: Subject to any disclaimer, the term of this patent is extended or adjusted under 35 U.S.C. 154(b) by 72 days.

(21) Appl. No.: 14/848,188

(22) Filed: Sep. 8, 2015

Related U.S. Application Data

(63) Continuation-in-part of application No. PCT/CA2014/000111, filed on Feb. 14, 2014.

(60) Provisional application No. 62/047,770, filed on Sep. 9, 2014.

(51) Int. Cl.
| | |
|---|---|
| *A61B 6/14* | (2006.01) |
| *A61B 6/00* | (2006.01) |
| *G01T 7/00* | (2006.01) |

(52) U.S. Cl.
CPC .............. *A61B 6/583* (2013.01); *G01T 7/005* (2013.01); *A61B 6/14* (2013.01)

(58) Field of Classification Search
CPC ........... A61B 6/14; A61B 6/44; A61B 6/4429; A61B 6/58; A61B 6/582; A61B 6/583; A61B 6/585; G01N 2223/3035
See application file for complete search history.

(56) References Cited

U.S. PATENT DOCUMENTS

| | | | |
|---|---|---|---|
| 4,638,502 A | 1/1987 | Yaffe | |
| 5,236,363 A | 8/1993 | Sandrik et al. | |
| 5,335,260 A | 8/1994 | Arnold | |
| 5,493,601 A | 2/1996 | Fivez et al. | |
| 5,539,799 A * | 7/1996 | Schulze-Ganzlin | ..... A61B 6/14 378/18 |
| 5,651,046 A | 7/1997 | Floyd et al. | |

(Continued)

FOREIGN PATENT DOCUMENTS

| | | |
|---|---|---|
| CA | 2419483 A1 | 3/2002 |
| GB | 2449113 A | 11/2008 |

(Continued)

OTHER PUBLICATIONS

AAPM Report No. 6, "Instrumentation Requirements of Diagnostic Radiological Physicists", 1998, 16 pages, Medical Physics Publishing, USA.

(Continued)

*Primary Examiner* — Thomas R Artman
(74) *Attorney, Agent, or Firm* — Michael R. Schacht; Schacht Law Offices, Inc.

(57) ABSTRACT

A phantom assembly for testing x-ray equipment comprising a phantom assembly for testing x-ray equipment comprising at least one image plate made of at least one image plate material, at least one base member made of at least one base material, at least one step surface formed in the base member, and at least one mesh insert. The at least one base material is selected, sized, and dimensioned such that base member yields a transmitted reference signal in addition to at least one transmitted energy test spectrum associated with the at least one step surface. The at least one mesh insert is selected, sized, and dimensioned such that the at least one mesh insert yields a transmitted energy resolution signal.

21 Claims, 27 Drawing Sheets

(56) References Cited

U.S. PATENT DOCUMENTS

| | | | |
|---|---|---|---|
| 5,841,835 | A | 11/1998 | Aufrichtig et al. |
| 5,910,975 | A | 6/1999 | Floyd et al. |
| 6,231,231 | B1 | 5/2001 | Farrokhnia et al. |
| 6,315,447 | B1 | 11/2001 | Nord et al. |
| 6,409,383 | B1 | 6/2002 | Wang et al. |
| 6,488,409 | B1 | 12/2002 | Vafi et al. |
| 6,632,020 | B2 | 10/2003 | Kaufhold et al. |
| 6,811,310 | B2 | 11/2004 | Lang et al. |
| 6,905,245 | B2 | 6/2005 | Cresens |
| 6,979,124 | B2 | 12/2005 | Gerwin et al. |
| 6,997,610 | B2 | 2/2006 | Heismann |
| 7,039,163 | B2 | 5/2006 | Popescu et al. |
| 7,056,019 | B1 | 6/2006 | Hanson et al. |
| 7,056,020 | B2 | 6/2006 | Saunders et al. |
| 7,173,238 | B2 | 2/2007 | Karasawa |
| 7,256,392 | B2 | 8/2007 | Sendai et al. |
| 7,391,892 | B2 | 6/2008 | Gerwin |
| 7,471,761 | B2 * | 12/2008 | Michaeli .................. A61B 6/14 378/38 |
| 7,503,694 | B2 * | 3/2009 | Gray ...................... G03B 42/02 378/204 |
| 7,510,325 | B2 | 3/2009 | Endo et al. |
| 7,539,284 | B2 | 5/2009 | Besson |
| 7,545,964 | B2 | 6/2009 | Lang et al. |
| 7,642,506 | B2 | 1/2010 | Wang et al. |
| 7,728,285 | B2 | 6/2010 | Suh et al. |
| 7,729,524 | B2 | 6/2010 | Rogers et al. |
| 7,950,849 | B2 | 5/2011 | Claus et al. |
| 8,000,441 | B2 | 8/2011 | Lang et al. |
| 8,308,362 | B2 * | 11/2012 | Dove ..................... A61B 6/145 378/204 |
| 8,708,562 | B1 * | 4/2014 | Nosil ..................... A61B 6/583 378/207 |
| 9,329,141 | B2 * | 5/2016 | Stutman ............... G01N 23/046 |
| 2002/0061502 | A1 | 5/2002 | Persohn et al. |
| 2005/0077459 | A1 | 4/2005 | Engler et al. |
| 2005/0123093 | A1 | 6/2005 | Lawaczeck et al. |
| 2007/0058786 | A1 * | 3/2007 | Michael .................. A61B 6/14 378/207 |
| 2007/0183590 | A1 | 8/2007 | Gray |
| 2008/0219412 | A1 | 9/2008 | Lang |
| 2008/0298540 | A1 | 12/2008 | Serban et al. |
| 2011/0096911 | A1 | 4/2011 | Dove et al. |
| 2014/0226782 | A1 * | 8/2014 | Stutman ............... G01N 23/046 378/4 |

FOREIGN PATENT DOCUMENTS

| | | |
|---|---|---|
| WO | 2008124649 A2 | 10/2008 |
| WO | 2011029910 A1 | 3/2011 |

OTHER PUBLICATIONS

ACR Phantom, Geometry I—ACR Type Radiography, predates Mar. 5, 2012, 1 page.

Cardinal Health, Nuclear Associates 76-025 CDHR Dental Image Quality Test Tool Instruction Manual, 2004, 10 pages.

CDRH drawing of the CDRH Dental Phantom, Jan. 10, 1993, 5 pages.

Conway et al., Medical Physics, "Beam quality independent attenuation phantom for estimating patient exposure from x-ray automatic exposure controlled chest examinations", 1984, 1 page, vol. 11, No. 6, Center for Devices and Radiological Health, Food and Drug Administration, Rockville, MD.

FDA, http://www.fda.gov/Radiation-EmittingProducts/RadiationSafety/NationwideEvaluationofX-RayTrendsNEXT/ucm116509.htm, Dental NEXT Surveys of 1993 and 1999, 1 page.

Fluke Biomedical, 76-025 CDRH Dental Image Quality Test Tool, 2004, 2 pages.

IAEA, Phantom Photo only, 2005, 1 page.

IAEA, Radiation Protection of Patients (RPOP), 2005, 7 pages.

IBA, Quality Control in Medical Imaging, 2011, 3 pages.

International Searching Authority, "ISR PCT/CA2014/000111", May 6, 2014, 9 pages.

Leeds Test Objects Ltd., TOR DEN Digital Dental Specifications, 2011, 2 pages.

Leeds Test Objects Sales Specifications, "medical imaging phantoms", Nov. 16, 2010 12 pages, North Yorkshire, UK.

Mah et al., Quality assurance phantom for digital dental imaging, Oral Surgery, Oral Medicine, Oral Pathology, Oral Radiology, and Endodontology: Oral and Maxillofacial Radiology, vol. 112, No. 5, Nov. 2011, 8 pages.

Medical Device Agency (MDA), Evaluation Report No. MDA/95/27, FAXIL Evaluation Report, Appendix A:1, Mar. 1995, 3 pages.

Nationwide Evaluation of X-Ray Trends (NEXT), Tabulation and Graphical Summary of the 1999 Dental Radiography Survey, Aug. 2007, 83 pages.

NEXT, CDRH Dental Image Quality Test Tool, Nuclear Associates Diagnostic Radiology and Radiation Therapy Catalog, 2004, 2 pages.

NEXT99Dental, Appendix A: Diagram of Dental Phantom and Optical Density and Image Quality, Aug. 2007, 2 pages.

Photo Doc 1P1040028, predates Mar. 5, 2012, 1 page.

PTW, Solutions Catalog, Radiation Medicine QA, 2012, 168 pages.

Quart, Dental X-Ray QA/QC Test Phantoms, 1998, 4 pages.

Scanditronix Wellhofer Product Catalogue, "Quality Assurance in Digital Radiology: Measuring Instruments and Test Devices Main Products", Aug. 2006, pp. 6, 8, Germany, TN, Sweden, China.

Scanditronix Wellhofer, Kompaktkurs R-PAL-1 Konstanzprufung nach 16 RoV, Jan. 5, 2003, 25 pages.

Scanditronix, Wellhofer Attenuator Photo, predates Mar. 5, 2012, 1 page.

Schueler et al., Presentation "Use of the R/F Accreditation Phantom for Fluoroscopic System Evaluation", Jun. 2001, 56 pages.

Servomaa et al., BIR Report 18: Technical and Physical Parameters for Quality Assurance in Medical Diagnostic Radiology, "Patient equivalent phantoms in chest radiography", 1989, 4 pages, British Institute of Radiology, London.

Wilson et al., American College of Radiology, "Radiography Fluoroscopic Phantom", Jun. 2001, 8 pages, Medical Physics Publishing, USA.

Yoshiura et al., Assessment of image quality in dental radiography, part 1: phantom validity, 1999, 2 pages.

Yoshiura et al., Assessment of image quality in dental radiography, part 2: optimum exposure conditions for detection of small mass changes in 6 intraoral radiography systems, 1999, 2 pages.

* cited by examiner

Place phantom

Slide in detector

Flip over

Conduct tube

Start exposure

Bitewing set up

Positioning done
(vertical option)

Remove detector

Start exposure

Bitewing setup

Lower tube (horizontal option)

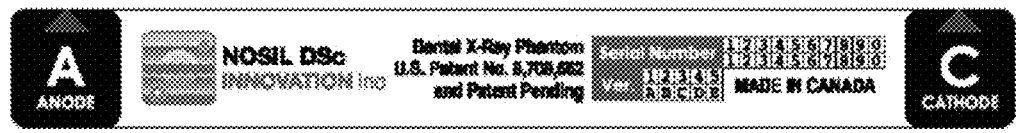
FIG. 35
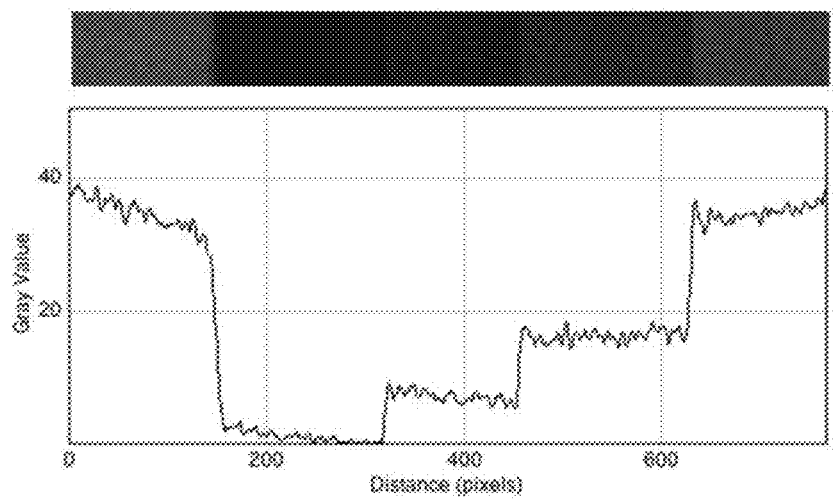
FIG. 36  145px  173px  135px  173px  136px
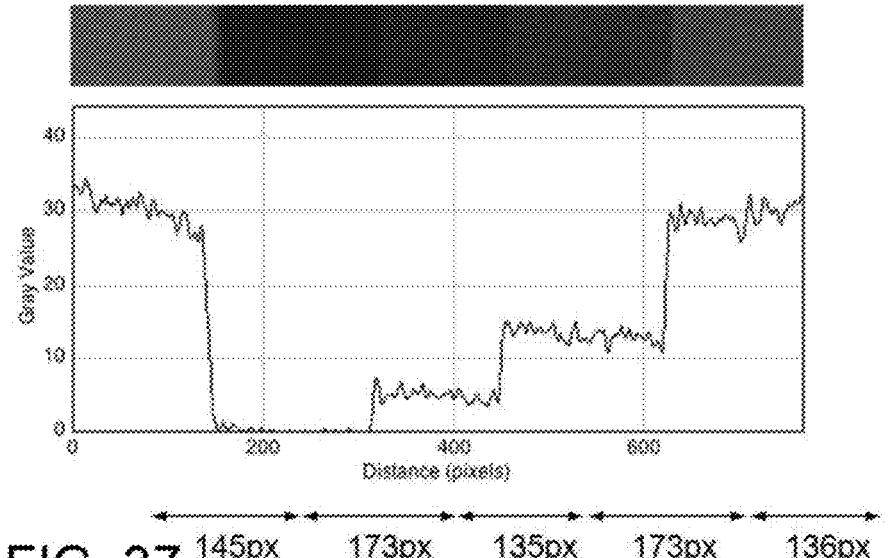
FIG. 37  145px  173px  135px  173px  136px

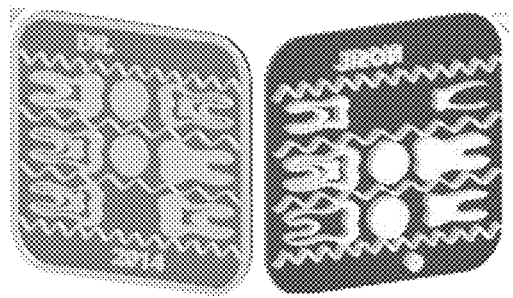
FIG. 43A  
Front side
FIG. 43B  
Back side
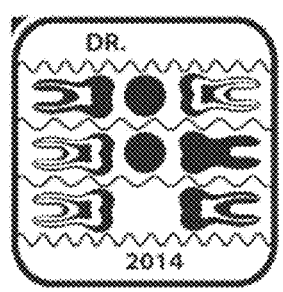
FIG. 44A
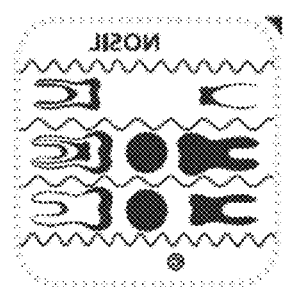
FIG. 44B
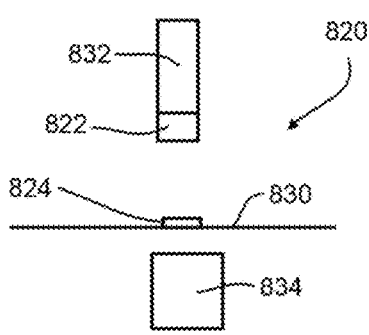
FIG. 45
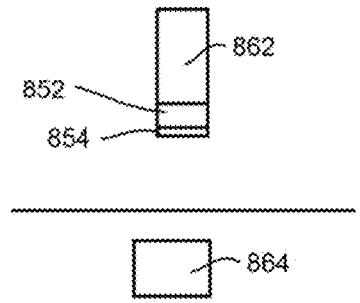
FIG. 46

PHANTOM SYSTEMS AND METHODS FOR DIAGNOSTIC RADIOGRAPHIC AND FLUOROSCOPIC X-RAY EQUIPMENT

RELATED APPLICATIONS

This application, U.S. patent application Ser. No. 14/848,188 filed Sep. 8, 2015, is a continuation-in-part of International PCT Application No. PCT/CA2014/000111 filed Feb. 14, 2014, now expired.

International PCT Application No. PCT/CA2014/000111 claims priority of U.S. patent application Ser. No. 13/786,285 filed Mar. 5, 2013, now U.S. Pat. No. 8,708,562 which issued on Apr. 29, 2014.

This application also claims benefit of U.S. Provisional Application Ser. No. 62/047,770 filed Sep. 9, 2014.

The contents of all related applications cited above are incorporated herein by reference.

TECHNICAL FIELD

The present invention relates to the assessment of diagnostic radiography or fluoroscopy (radioscopy) equipment and, more particularly, to systems and methods for determining the quality of diagnostic radiography or fluoroscopy (radioscopy) equipment.

BACKGROUND

Quality Assurance (QA) of diagnostic equipment such as x-ray equipment (radiography) and fluoroscopy (radioscopy) is necessary to ensure the production of high quality diagnostic information via x-ray images. Both initial acceptance testing and periodic routine examinations are part of quality assurance. The present invention has application to both radiographic and fluoroscopic commercial x-ray equipment, but will be described herein in the context of radiographic equipment.

The term "phantom" is typically applied to a device that is used for acceptance testing and routine ongoing testing of diagnostic x-ray equipment. In particular, a phantom is a device used to determine image quality and patient dose under clinical conditions. In addition to the phantom, certain other x-ray test equipment is necessary for Quality Assurance. Acceptance testing and the provision of a suitable on-going testing routine are typically the responsibility of a qualified medical physicist. Periodic quality assurance using the prescribed testing routine is typically the responsibility of a designated and trained x-ray technologist.

A number of testing phantoms is available commercially: each has its recommended testing routine. The American College of Radiology has created a set of Accreditation Program Requirements and developed a phantom (the ACR phantom) that is commonly used according to those requirements for acceptance and ongoing testing of x-ray equipment. The ACR phantom produces information that allows the accurate assessment of the diagnostic quality of images produced by a medical x-ray unit.

The need thus exists for phantom systems and methods that allow the accurate assessment of the diagnostic quality of images produced by a medical x-ray unit but which are light, have a small form factor, and are convenient to use.

SUMMARY

The present invention may be embodied as a phantom assembly for testing x-ray equipment comprising a phantom assembly for testing x-ray equipment comprising at least one image plate made of at least one image plate material, at least one base member made of at least one base material, at least one step surface formed in the base member, and at least one mesh insert. The at least one base material is selected, sized, and dimensioned such that base member yields a transmitted reference signal in addition to at least one transmitted energy test spectrum associated with the at least one step surface. The at least one mesh insert is selected, sized, and dimensioned such that the at least one mesh insert yields a transmitted energy resolution signal.

BRIEF DESCRIPTION OF THE DRAWINGS

FIG. 35 depicts an example label that may be used by the example dental test phantom of the present invention;

FIGS. 36-42 contain example images and charts associated with test images created using the example dental test phantom of the present invention;

FIGS. 43A and 43B depict the graphics formed on the front and back sides, respectively, of the example image plate of the example dental test phantom;

FIGS. 44A and 44B depict the images generated by the front and back sides, respectively, when the example image plate of FIG. 42 is used as part of the example dental test phantom of the present invention; and FIGS. 45 and 46 are highly schematic elevation views illustrating the use of two more example test phantoms of the present invention.

DETAILED DESCRIPTION

A phantom system constructed in accordance with, and embodying, the principles of the present invention may be embodied in a number of ways with certain parts common to the different embodiments. A number of examples of embodiments of phantom systems of the present invention will be presented below, followed by general explanations of the use of these phantom systems.

Additionally, the example phantoms of the present invention as described herein have application to both radiographic and fluoroscopic x-ray equipment. For the most part, the present invention has been discussed herein in the context of radiographic equipment for simplicity, but it should be understood that any reference to radiographic equipment may also refer to fluoroscopic equipment, and vice versa.

I. First Example Phantom System

Figure 1:
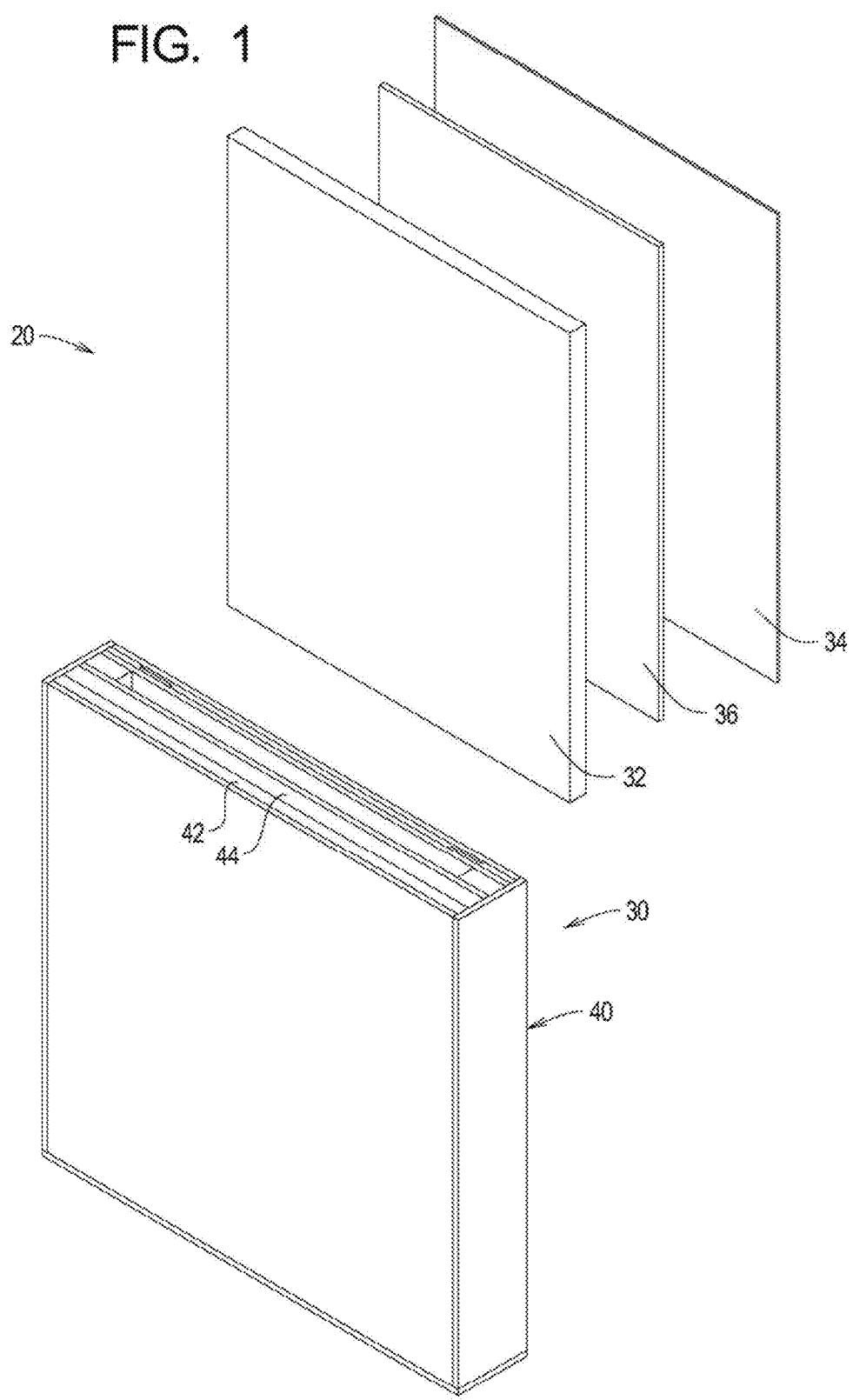
FIG. 1 is an exploded, perspective view of a first example phantom system of the present invention.

Referring initially to FIG. 1 of the drawing, a first example phantom system 20 is depicted therein. The first example phantom system 20 comprises a base assembly 30, a first plate 32, a second plate 34, and a third plate 36. The example base assembly 30 comprises a housing assembly 40, an image plate 42, and a base plate 44. The example image plate 42 and base plate 44 are integrally formed with the example housing assembly 40, but it may be possible to construct the base assembly 30 such that the image plate 42 and/or base plate 44 are detachably attached from the housing assembly 40.

Figure 2:
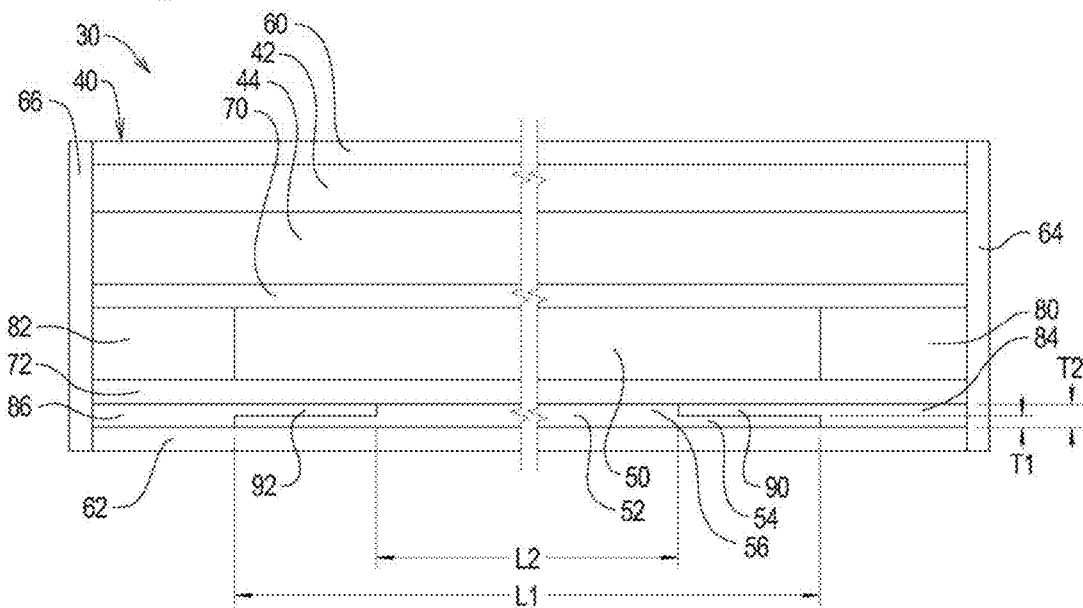
FIG. 2 is a partial plan view illustrating the first example phantom system in a first configuration.

As perhaps best shown in FIG. 2 of the drawing, the example base assembly 30 defines a first cavity 50 and a second cavity 52. The example second cavity 52 further defines a first portion 54 and a second portion 56. In particular, the first portion 54 of the second cavity 52 has a thickness T1 and a length L1. The second portion 56 of the second cavity 52 has a thickness T2 and a length L2. The first cavity portion 54 is thus wider and thinner than the second cavity portion 56.

The first example phantom system 20 is configured to operate in first, second, third, and fourth configurations. In the first configuration (best shown in FIG. 2), the base assembly 30 is used without any of the first, second, or third plates 32, 34, or 36, and the first and second cavities 50 and 52 are empty. The first example phantom system 20 in the first configuration is used to perform a chest image quality test.

Figure 3:
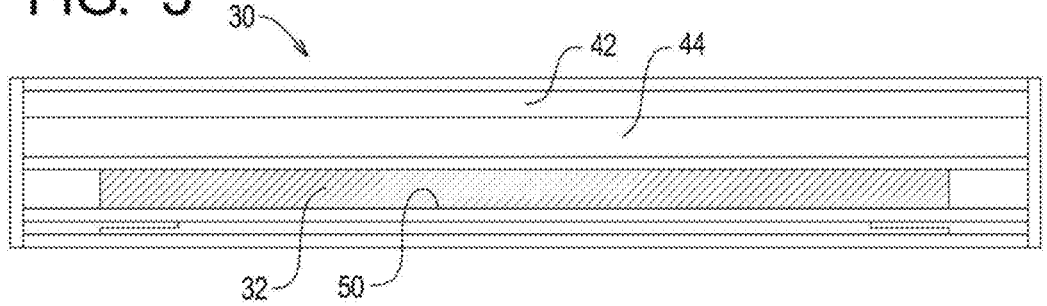
FIGS. 3, 4, and 5 are plan views similar to FIG. 2 illustrating the first example phantom system in a second, third, and fourth configurations.

In the second configuration (shown in FIG. 3), the base assembly 30 is used in conjunction with the first plate 32. In particular, the first plate 32 is inserted into the first cavity 50. The first example phantom system 20 in the second configuration is used to perform an abdomen image quality test.

Figure 4:
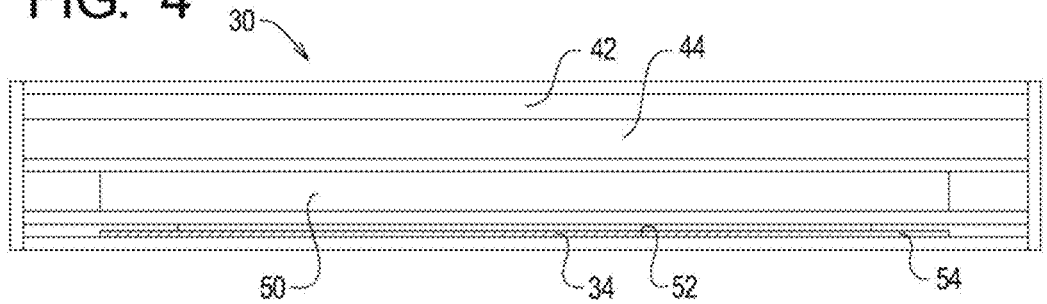

In the third configuration (shown in FIG. 4), the base assembly 30 is used in conjunction with the second plate 34. In particular, the second plate 34 is inserted into the first portion 54 of the second cavity 52. The second plate 34 is wider and thinner than the third plate 36. As discussed above, the first cavity portion 54 is similarly wider and thinner than the second cavity portion 56. Accordingly, only one of the second and third plates 34 and 36 may be inserted into the second cavity 52 at a time. The first example phantom system 20 in the third configuration is used to perform a chest doserate test.

Figure 5:
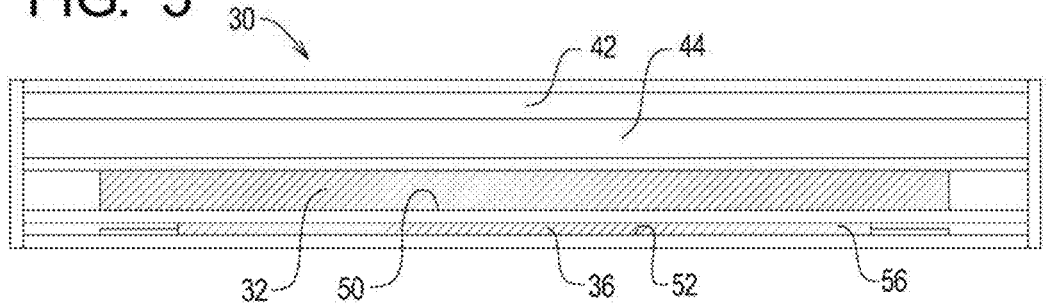

In the fourth configuration (shown in FIG. 5), the base assembly 30 is used in conjunction with the first plate 32 and the third plate 36. In particular, the first plate 32 is inserted into the first cavity 50 and the third plate 36 is inserted into the second portion 56 of the second cavity 52. Again, only one of the second and third plates 34 and 36 may be inserted into the second cavity 52 at a time. The first example phantom system 20 in the fourth configuration is used to perform an abdomen dose or doserate test.

Figure 6:
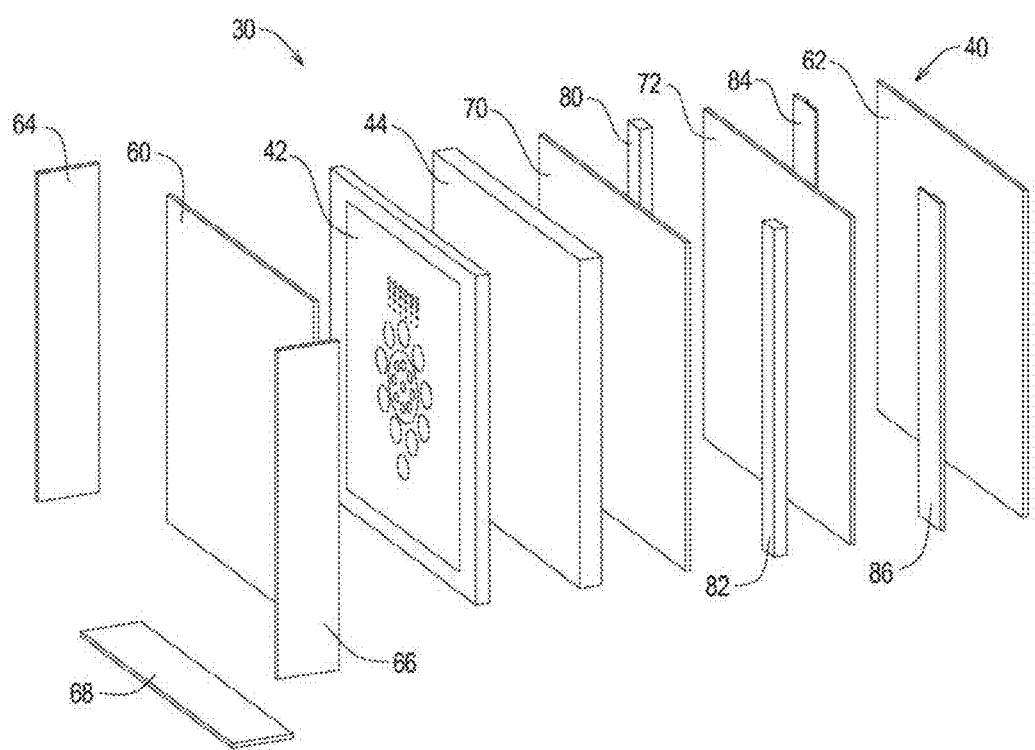
FIG. 6 is an exploded view of the base assembly of the first example phantom system.

FIGS. 2 and 6 of the drawing illustrates that the example housing assembly 40 of the example base assembly 30 comprises a first face cover sheet 60, a second face cover sheet 62, a first side cover sheet 64, a second side cover sheet 66, and an end cover sheet 68. FIGS. 2 and 6 further show that the example housing assembly 40 comprises a first spacer sheet 70, a second spacer sheet 72, a first spacer bar 80, a second spacer bar 82, a third spacer bar 84, and a fourth spacer bar 86. The third spacer bar 84 defines a first shoulder portion 90, while the fourth spacer bar 86 defines a second shoulder portion 92.

In the example base assembly 30, the image plate 42 is arranged between the first face cover sheet 60 and the base plate 44. In turn, the base plate 44 is arranged between the image plate 42 and the first spacer sheet 70. The first and second spacer bars 80 and 82 are arranged between the first and second spacer sheets 70 and 72 to define the first cavity 50. The third and fourth spacer bars 84 and 86 are arranged between the second spacer sheet 72 and the second face cover sheet 62 to define the second cavity 50. The first and second shoulder portions 90 and 92 of the third and fourth spacer bars 84 and 86 function to define the first and second cavity portions 54 and 56 of the second cavity 52.

The first and second side cover sheets 64 and 66 and the end cover sheet 68 are arranged to cover edges of the image plate 42 and base plate 44, face cover sheets 60 and 62, spacer sheets 70 and 72, and spacer bars 80, 82, 84, and 86. In the first example base assembly 30, adhesives are used to adhere the various plates, sheets, and spacer bars together.

The example first example phantom system 20 comprises an image plate 42, a base plate 44, a first plate 32, a second plate 34, and a third plate 36. Although the first example phantom system 20 comprises three plates, the advantages of the present invention may be realized using as few as one or two plates, and it may be possible to incorporate additional plates for additional test scenarios. Further, while the example image plate 42 and example base plate 44 are integrally formed with the housing assembly 40, one or both of the image plate 42 and base plate 44 may be removed from the housing assembly 40 as generally described above.

Figure 7:
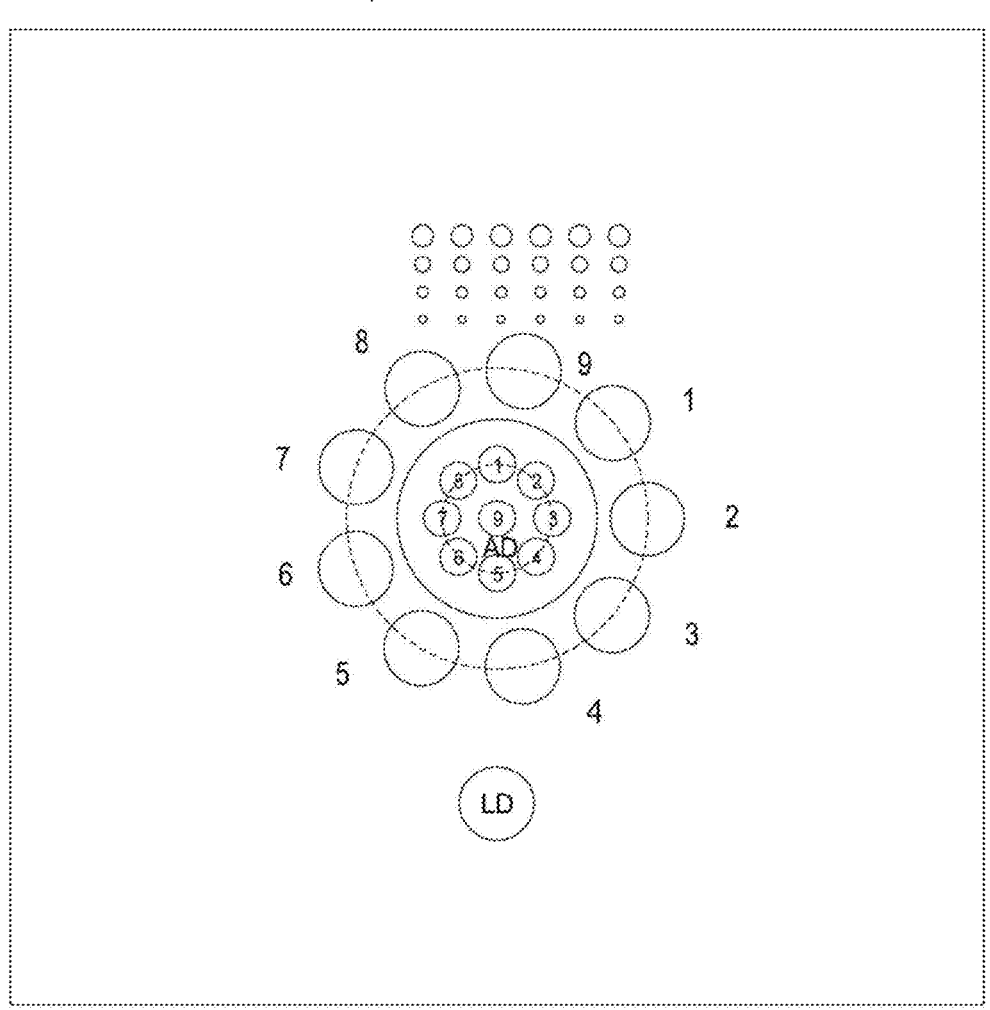
FIG. 7 is a plan view of a first image plate that may be used by a phantom system of the present invention.

The example image plate 42 is a conventional ACR image plate and contains structures that produce images that allow the image quality of the unit under test to be evaluated. The example image plate 42 comprises a 9.5 mm thick slab of Polymethylmethacrylate-Acrylic (PMMA) and image quality structures configured to result in an image that allows the evaluation of image quality characteristics such as high contrast resolution, low contrast resolution, low contrast details, and dynamic range (latitude). Details of a first example image plate 42 are shown in FIGS. 6 and 7.

The example image plate 42 allows high contrast image resolution to be evaluated from images representing 1.9 cm diameter copper mesh structures embedded in the PMMA slab at a depth of 5 mm. The mesh structures are formed in a range of mesh sizes. As one example, the mesh structures may range in size from 0.5 lp/mm to 3.2 lp/mm in nine steps. In the example image plate 42, the wires in the mesh structures are aligned at 45° to the cathode/anode direction. With the ACR image plate, the copper mesh structures are positioned in order of the size of the mesh and decreases in size in the clock-wise direction.

Low contrast resolution is evaluated from the images of nine holes in a 2 mm thick 1100 aluminum disc centered in the PMMA slab. In the example image plate 42, the holes have depths in the range of 0.1 mm to 1.7 mm. With the ACR image plate, the holes for determining low contrast resolution are positioned in order of the depth of the hole.

The contrast detail area may comprise four rows of six holes in the PMMA slab. In the example image plate 42, the holes in each row are of the same diameter, but the depths range from 0.3 mm to 1.5 mm in six steps, and the holes in the four rows range from 1.9 mm to 5.5 mm in diameter. With the ACR image plate, the holes for determining contrast detail are positioned in order of the depth of the hole.

The dynamic range may be evaluated from the image of an aluminum disk embedded in the PMMA plate. In the example image plate 42, the aluminum disk has a diameter of 19.5 mm and a thickness of 6.34 mm.

Figure 8:
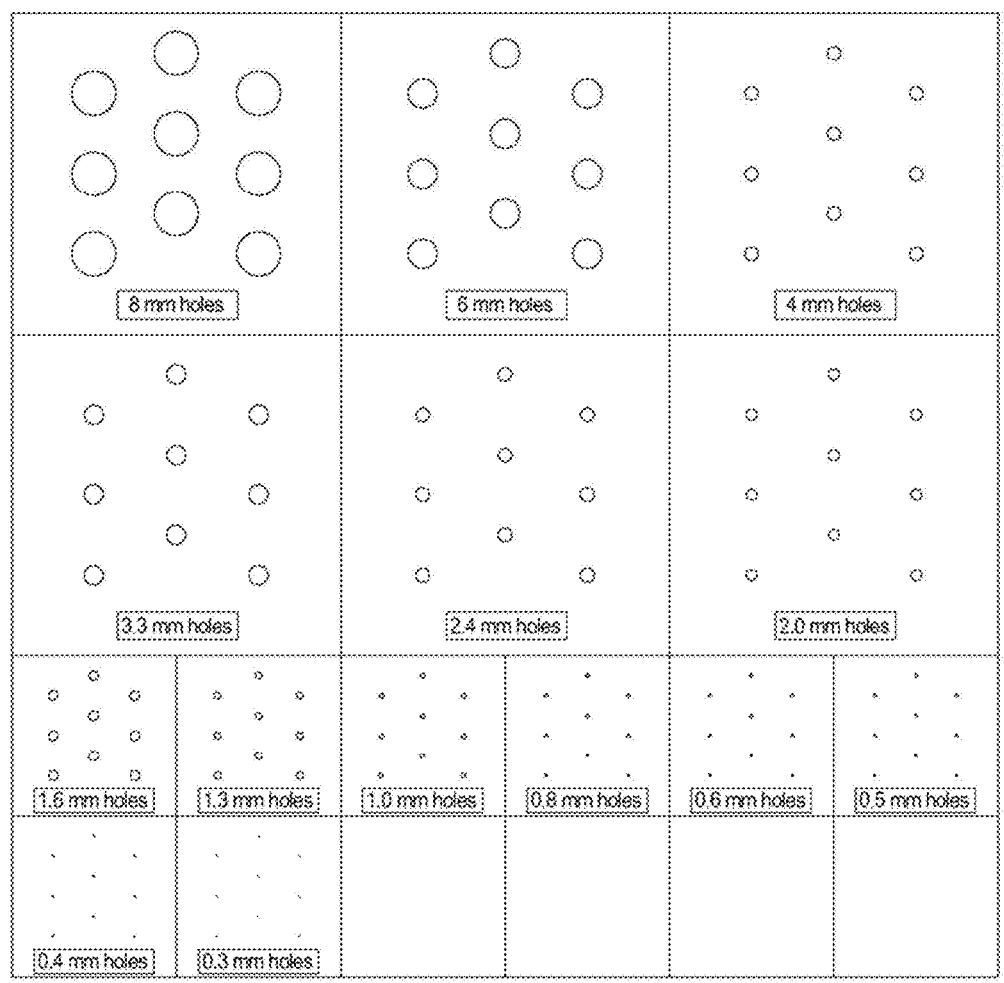
FIG. 8 is a plan view of a second image plate that may be used by a phantom system of the present invention.

A second example image plate 46 that may be used instead of or in conjunction with the example image plate 42 is depicted in FIG. 8 of the drawing. The second example image plate 46 comprises structures that produce images that allow the image quality of the unit under test to be evaluated. The example image plate 42 comprises a slab of material such as 1100 aluminum and image quality structures configured to result in an image that allows the evaluation of image quality characteristics such as high contrast resolution, low contrast resolution, low contrast details, and dynamic range (latitude).

In particular, the example image plate 46 defines six large square aluminum square portions and twelve aluminum square portions arranged in the PMMA slab. Each of the large and small square portions contains nine holes all having the same diameter and different depths. The depths of the holes are randomly formed so that a technician must determine which hole is deeper by analysis. In addition, the spaces or positions (x, y position) between holes may be randomized. The random depths and spacing prevent an analyst, such as a radiologist, QC technologist, or service engineer, from reaching a predetermined conclusion on contrast resolution and contrast detail based on the sequential arrangement of the hole depths in the given square portions and not on a visual analysis of the actual image. To ensure randomness, a random number generator may be used to determine hole depths and placement. The example image plate 46 may be provided with mesh structures and other features to allow further analysis of the x-ray equipment forming the image.

The base plate 44 may be referred to as a base spectral plate and is formed of materials configured such that the energy spectrum transmitted through the base plate 44 is similar to that of the conventional ACR phantom. Or stated alternatively, the energy spectrum transmitted through the base plate should be similar or analogous to a first or chest reference energy spectrum translated through a typical human chest. The Applicant has determined that the energy spectrum transmitted by the ACR phantom, and thus the chest reference energy spectrum, may be duplicated or emulated using, as one example, an 18.7 mm thick assembly comprising 4 slabs of polyvinyl chloride (PVC) (totaling 12.7 mm thick) and two slabs of Acrylonitrile butadiene styrene (ABS) (totaling 6 mm thick). Other materials and/or combinations of materials that yield a transmitted energy spectrum similar to a chest reference energy spectrum may be used in place of the PVC and ABS slabs described herein.

The first plate 32 may be referred to as an abdomen attenuation plate. The example first plate 32 comprises two 3 mm thick slabs of 1100 aluminum and two 3 mm thick slabs of ABS. When the first plate 32 is used in combination with the image plate 42 and the base plate 44 (i.e., second configuration FIG. 3), the resulting total x-ray attenuation is similar to that of the ACR phantom configured to emulate the human abdomen and thereby yield a spectral response analogous to a second or abdomen reference energy spectrum corresponding to that of a typical human abdomen. The transmitted doserate is, however, considerably greater. Another material or combination of materials that, in combination with the image plate 42 and the base plate 44, yield a total x-ray attenuation similar to that of the ACR phantom configured to emulate an abdomen and thus yield a spectral response analogous to the abdomen reference energy spectrum associated with a typical human abdomen may be used in place of the aluminum and ABS slabs.

The second plate 34 may be referred to as a chest doserate plate. The example second insert is made of a single 0.8 mm thick plate of copper. When used in combination with the image plate 42 and the base plate 44 (i.e., third configuration FIG. 4), the resulting total x-ray doserate is similar to that transmitted by the typical human chest. Another material or combination of materials that, in combination with the image plate 42 and the base plate 44 yield a total x-ray doserate similar to that of the human chest may be used in place of the single copper plate.

The third plate 36 may be referred to as an abdomen doserate plate. The example third insert is made of a single 2.1 mm thick plate of copper. When used in combination with the image plate 42, the base plate 44, and the first plate 32 (i.e., fourth configuration FIG. 5), the resulting total x-ray doserate is similar to that transmitted by the human abdomen. Another material or combination of materials that, in combination with the image plate 42, the base plate 44, and first plate 32 yield a total x-ray doserate similar to that of the human abdomen may be used in place of the single copper plate.

To summarize then, the base plate 44 is made of at least one base material, the first plate 32 is made of at least one first plate material, the second plate 34 is made of at least one second plate material, and the third plate 36 is made of at least one third plate material. The at least one base material is selected, sized, and dimensioned such that the base plate 44, in combination with the image plate 42, yields a first transmitted energy spectrum that emulates a first reference energy spectrum associated with a human chest. The at least one first plate material is selected, sized, and dimensioned such that the first plate 32, in combination with the image plate 42 and the base plate 44, yields a second transmitted energy spectrum that emulates a second reference energy spectrum associated with a human abdomen. The at least one second plate material is selected, sized, and dimensioned such that the second plate 34, in combination with the image plate 42 and the base plate 44, yields a first transmitted doserate that emulates a first reference doserate associated with a human chest. The at least one third plate material is selected, sized, and dimensioned such that the third plate 36, in combination with the image plate 42, the base plate 44, and the first plate 32 yields a second transmitted doserate that emulates a second reference doserate associated with a human abdomen.

In addition, the form factor of the first example phantom system 20 can be 25 cm by 25 cm in area and 4.6 cm in total thickness. With this form factor and the materials forming the base assembly 30 and plates 32, 34, and 36 as described above, the total weight of all of the components of the first example phantom system 20 can be as little as approximately 7 lbs (3.2 kg).

II. Second Example Phantom System

Figure 9:
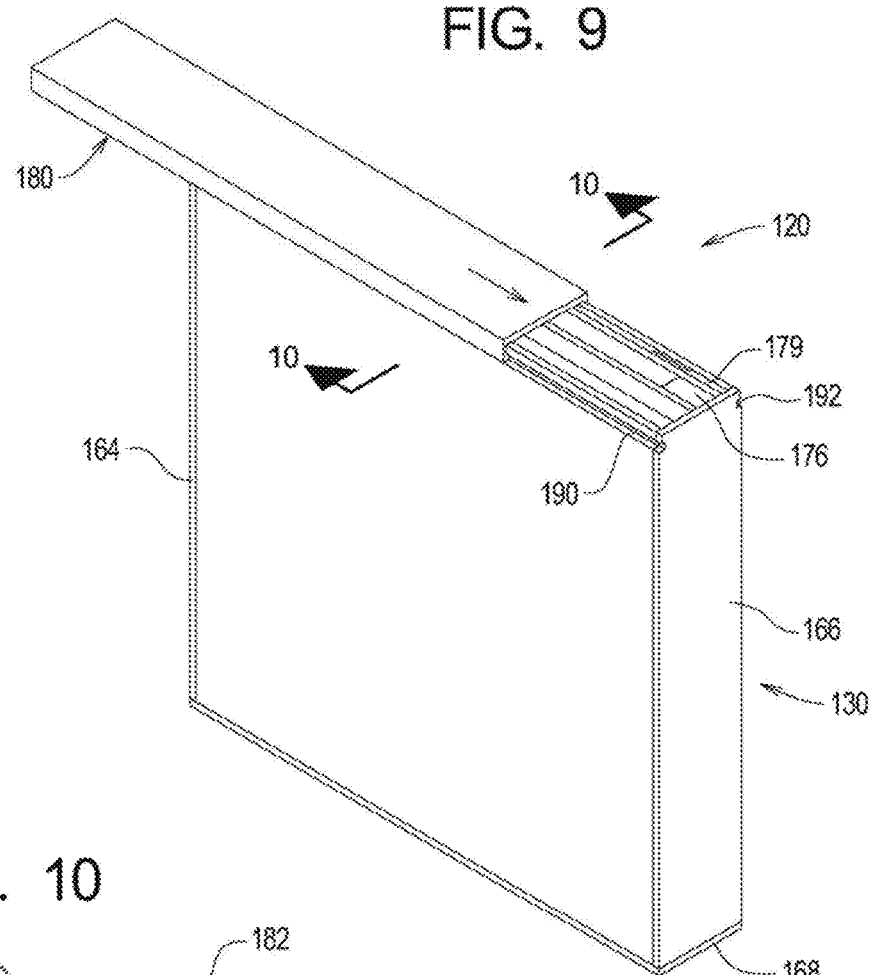
FIG. 9 is a perspective view of a second example base assembly of a second example phantom system of the present invention.
Figure 10:
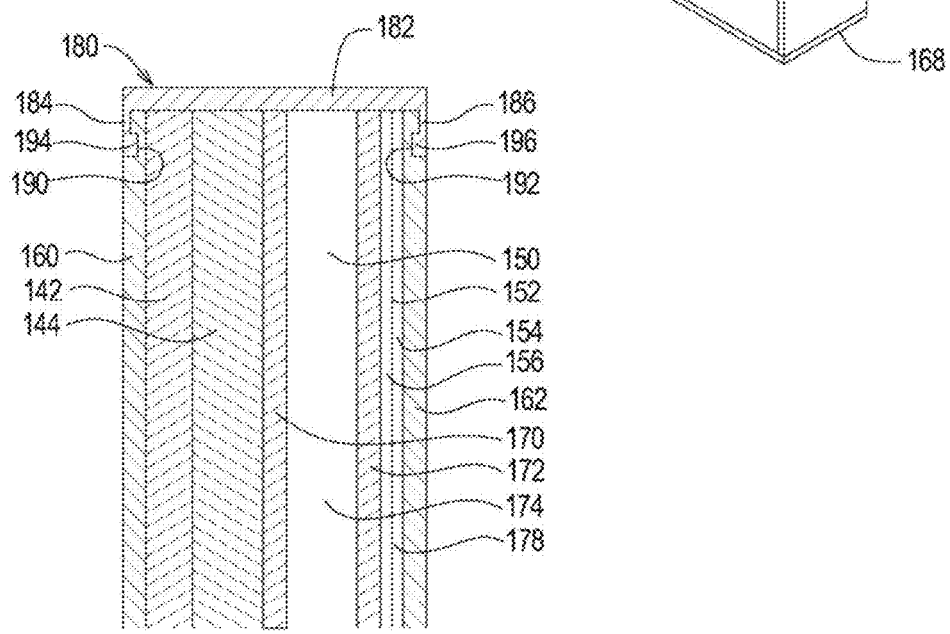
FIG. 10 is a section view taken along lines 10-10 in FIG. 9.
Figure 11:
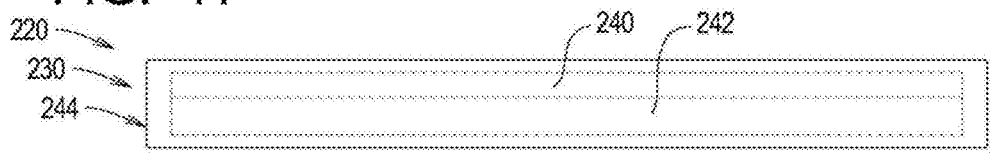
FIGS. 11-14 are plan views illustrating components that, when used together, form a third example phantom system of the present invention.
Figure 12:
Figure 13:
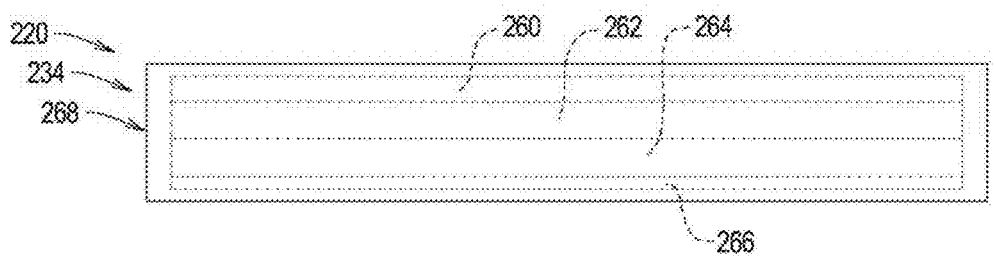

Referring now to FIGS. 9 and 10 of the drawing, a second example phantom system 120 is depicted therein. The second example phantom system 120 comprises a base assembly 130, a first plate, a second plate, and a third plate. The first, second, and third plates are not illustrated in FIGS. 9 and 10 but would be constructed and used in substantially the same manner as the first, second, and third plates 32, 34, and 36 described above. The example base assembly 130 comprises a housing assembly 140, an image plate 142 (not shown?), and a base plate 144.

The example housing assembly 140 defines a first cavity 150 and a second cavity 152. The example second cavity 152 further defines a first portion 154 and a second portion 156. As with the example cavity portions 54 and 56 described above, first cavity portion 154 is thus wider and thinner than the second cavity portion 152.

The second example phantom system 120 is configured to operate in first, second, third, and fourth configurations. In the first configuration, the base assembly 130 is used without any of the first, second, or third plates, and the first and second cavities 150 and 152 are empty. The first example phantom system 120 in the first configuration is used to perform a chest image quality test. In the second configuration, the base assembly 130 is used in conjunction with the first plate to perform an abdomen image quality test. In the third configuration, the base assembly 130 is used in conjunction with the second plate to perform a chest doserate test. In the fourth configuration, the base assembly 130 is used in conjunction with the first plate and the third plate to perform an abdomen dose or doserate test.

FIGS. 9 and 10 of the drawing illustrate that the example housing assembly 140 of the example base assembly 130 comprises a first face cover sheet 160, a second face cover sheet 162, a first side cover sheet 164, a second side cover sheet 166, and an end cover sheet 168. FIG. 6 further shows that the example housing assembly 140 comprises a first spacer sheet 170 and a second spacer sheet 172. First and third spacer bars 174 and 176 are visible in FIG. 10. Like the first example base assembly 30, the second example base assembly 130 comprises a second spacer bar 176 and a fourth spacer bar 179 visible in FIG. 9.

FIGS. 9 and 10 further illustrate that the second example housing assembly 130 further comprises a cover member 180. The example cover member 180 defines a cover portion 182, a first connecting portion 184, and a second connecting portion 186. Formed in the first and second face cover sheets 160 and 162 are first and second connecting grooves 190 and 192. First and second connecting projections 194 and 196 are formed on the first and second connecting portions 184 and 186, respectively. Further, the connecting grooves 190 and 192 and connecting projections 194 and 196 are complementary such that the grooves 190 and 192 receive the projections 194 and 196.

Accordingly, the cover member 180 may be detachably attached to the base assembly 130 by sliding the cover member 180 such that the connecting projections 194 and 196 are received by the connecting grooves 190 and 192. The cover member 180 inhibits access to and possible contamination of the first and second cavities 150 and 152.

Ideally, the second example housing assembly 130 comprising the cover member 180, the first plate, 132, second plate 134, and third plate 136 can easily be cleaned and sterilized (e.g., autoclaved) without damage.

III. Third Example Phantom System

Figure 14:
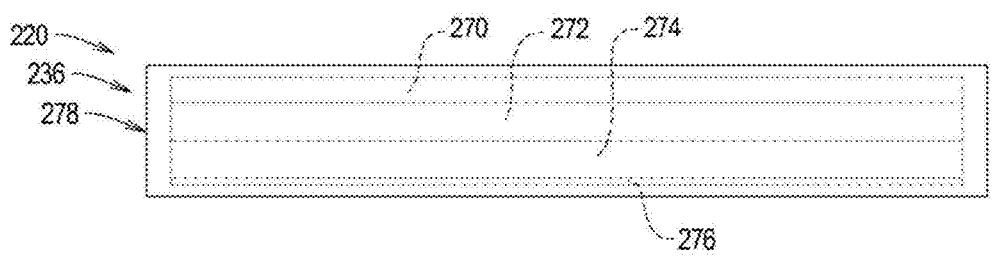
Figure 15:
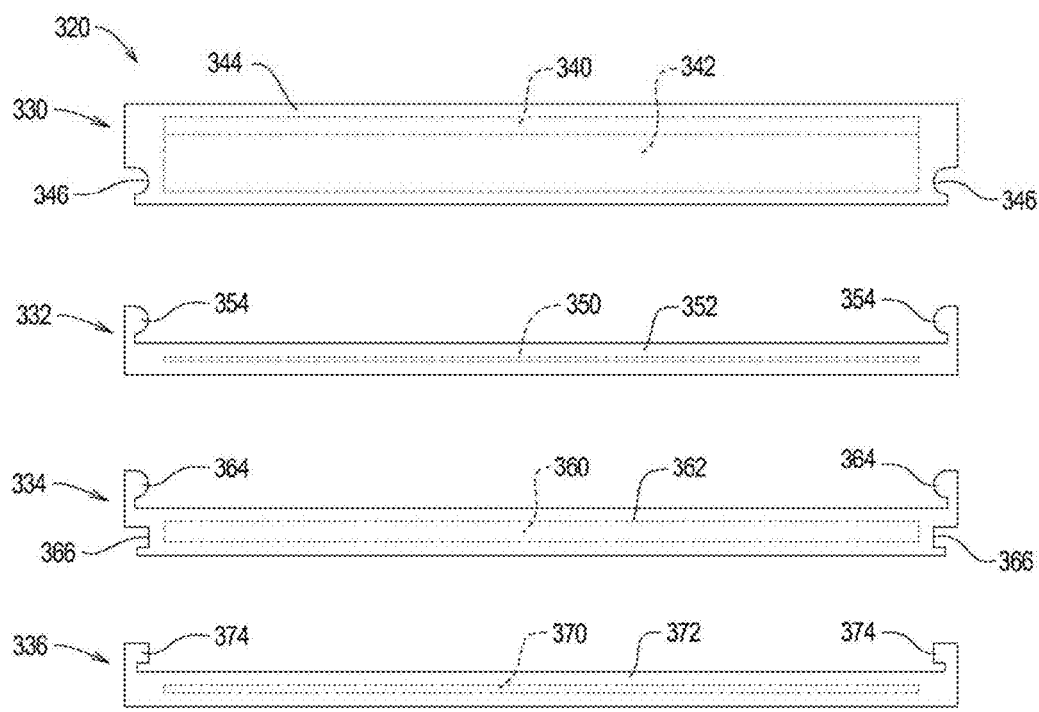
FIG. 15 is an exploded plan view of a fourth example phantom system of the present invention.
Figure 16:
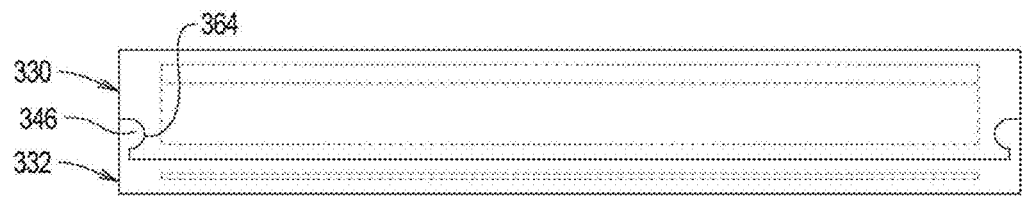
FIGS. 16-18 are plan views similar to FIG. 15 illustrating the fourth example phantom system in a second, third, and fourth configurations.
Figure 17:
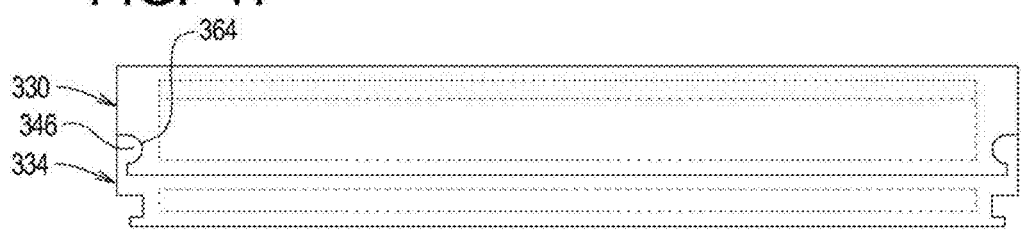
Figure 18:
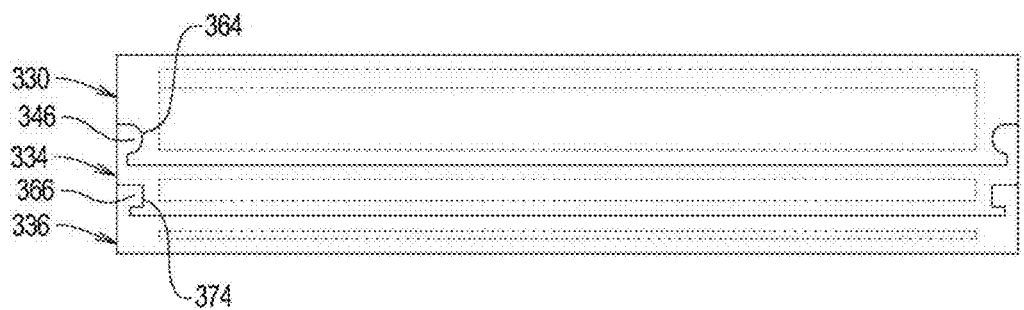

Referring now to FIGS. 11, 12, 13, and 14 of the drawing, depicted therein is a third example phantom system 220 of the present invention. The third example phantom system 220 comprises a first phantom assembly 230 (FIG. 11), a second phantom assembly 232 (FIG. 12), a third phantom assembly 234 (FIG. 13), and a fourth phantom assembly 236 (FIG. 14).

The first phantom assembly 230 (FIG. 11) comprises an image plate 240 and a first base plate 242 arranged within a first housing 244. The first base plate 242 may be integrally formed as part of the first housing 244. The second phantom assembly 232 (FIG. 12) comprises an image plate 250, a second base plate 252, a first plate 254, and a second housing 256. The second base plate 252 and first plate 254 may be integrally formed as part of the second housing 256. The third phantom assembly 234 (FIG. 13) comprises an image plate 260, a third base plate 262, a second plate 264, a third plate 266, and a third housing 268. The third base plate 262 and second plate 264 may be integrally formed as part of the third housing 268. The fourth phantom assembly 236 (FIG. 14) comprises an image plate 270, a fourth base plate 272, a fourth plate 274, a fifth plate 276, and a fourth housing 278. The fourth base plate 272 and fourth plate 274 may be integrally formed as part of the fourth housing 278.

The first, second, third, and fourth base plates 242, 252, 262, and 272 may be similar to the example base plate 42 described above. The first plate 254, second plate 264, and fourth plate 274 may be similar to the example first plate 32 described above. The example third plate 264 may be similar to the second plate 34 described above. The example fifth plate 276 may be similar to the third plate 36 described above.

The third example phantom system 220 is configured to operate in first, second, third, and fourth configurations. In the first configuration, the first phantom assembly 230 is used to perform a chest image quality test. In the second configuration, the second phantom assembly 232 is used to perform an abdomen image quality test. In the third configuration, the third phantom assembly 234 is used to perform a chest doserate test. In the fourth configuration, the fourth phantom assembly 236 is used to perform an abdomen dose or doserate test.

Ideally, the first, second, third, and fourth phantom assemblies 230, 232, 234, and 236 can easily be cleaned and sterilized (e.g., autoclaved) without damage.

IV. Fourth Example Phantom System

Referring now to FIGS. 15, 16, 17, and 18 of the drawing, depicted at 320 therein is a fourth example phantom system of the present invention. As perhaps best shown in FIG. 15, the fourth example phantom system 320 comprises a base assembly 330, a first plate assembly 332, a second plate assembly 334, and a third plate assembly 336.

The base assembly 330 comprises an image plate 340, a base plate 342, and a base housing 344. The base housing 344 defines base housing key slots 346. The base plate 342 may be integrally formed with the base housing 344. The first plate assembly 332 comprises a first plate 350 and a first plate housing 352. The first plate housing 352 defines first base housing key projections 354. The second plate assembly 334 comprises a second plate 360 and a second plate housing 362. The second plate housing 362 defines second base housing key projections 364 and extension housing key slots 366. The second plate 360 may be integrally formed with the second plate housing 362. The third plate assembly 336 comprises a third plate 370 and a third plate housing 372. Extension housing key projections 374 are formed on the third plate housing 372.

The base plate 342 may be similar to the example base plate 42 described above. The second plate 360 may be similar to the example first plate 32 described above. The example first plate 350 may be similar to the second plate 34 described above. The example third plate 370 may be similar to the third plate 36 described above.

The fourth example phantom system 320 is configured to operate in first, second, third, and fourth configurations. In the first configuration (FIG. 15), the base assembly 330 is used by itself to perform a chest image quality test.

In the second configuration (FIG. 16), the first plate assembly 332 is detachably attached to the base assembly 330 using the base housing key slots 346 and the first base housing key projections 354. In this second configuration, the first plate assembly 332 and base assembly 330 are used to perform a chest dose test.

In the third configuration (FIG. 17), the second plate assembly 334 is detachably attached to the base assembly 330 using the base housing key slots 346 and the second base housing key projections 364. The second plate assembly 334 and the base assembly 330 are used to perform a abdomen image quality test in the third configuration.

In the fourth configuration (FIG. 18), the second plate assembly 334 is detachably attached to the base assembly 330 using the base housing key slots 346 and the second base housing key projections 364, and the third plate assembly 336 is detachably attached to the second insert base assembly 334 using the extension housing key slots 366 and the extension housing key projections 374. In this fourth configuration, the base assembly 330, the second insert assembly 334, and the third insert assembly 336 are used to perform an abdomen dose or doserate test.

It should be noted that the relative positions of the various projections and slots may be exchanged without affecting the fundamental operation of the fourth example phantom system 320 as described below.

Ideally, the base assembly 330, first plate assembly 332, second plate assembly 334, and third plate assembly 336 can all be sterilized (e.g., autoclaved) without damage.

V. Fifth Example Phantom System

Figure 19:
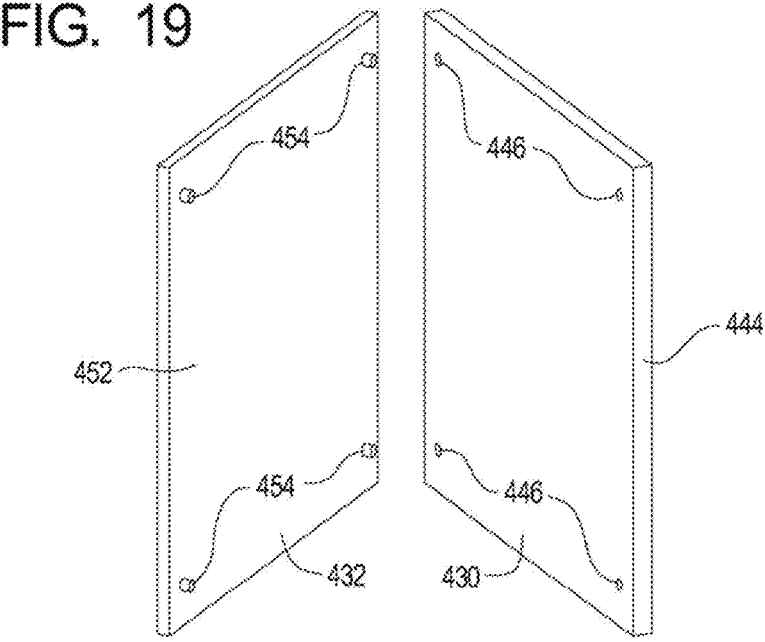
FIG. 19 is a perspective view depicting a portion of a fifth example phantom system of the present invention.
Figure 20:
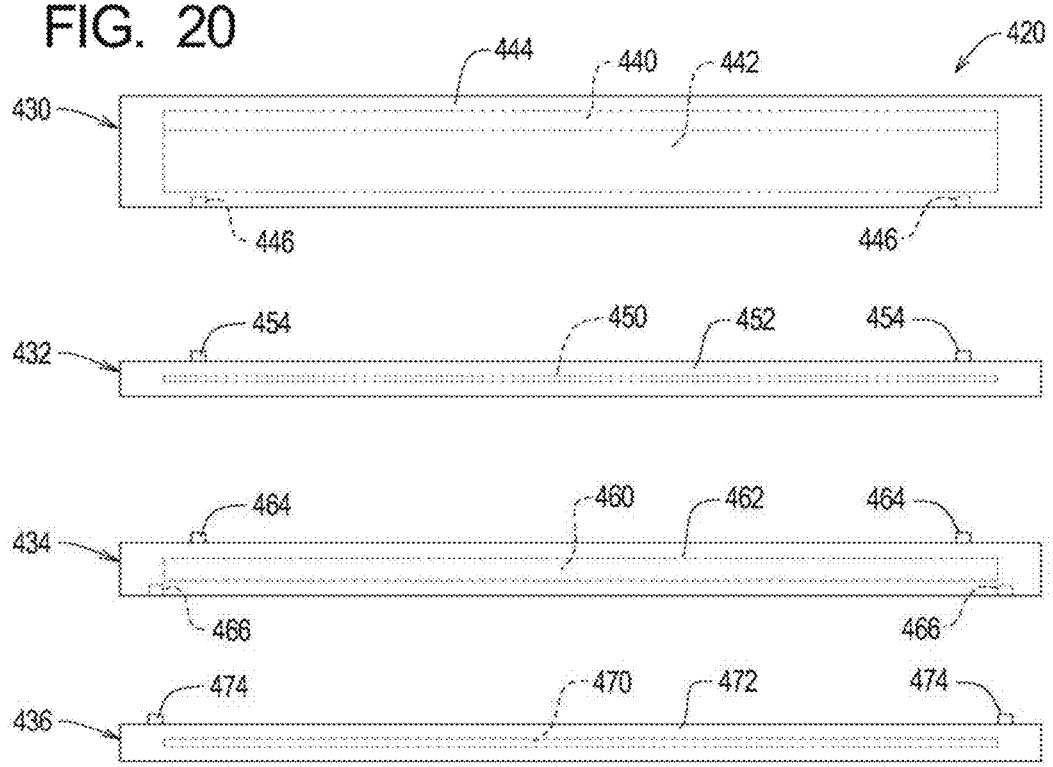
FIG. 20 is a plan view illustrating the fifth example phantom system of the present invention.

Referring now to FIGS. 19 and 20, depicted at 420 therein is a fifth example phantom system of the present invention. As shown in FIG. 20, the fifth example phantom system 420 comprises a base assembly 430, a first plate assembly 432, a second plate assembly 434, and a third plate assembly 436.

The base assembly 430 comprises an image plate 440, a base plate 442, and a base housing 444. The base housing 444 defines base housing key openings 446. The base plate 442 may be integrally formed with the base housing 444. The first plate assembly 432 comprises a first plate 450 and a first plate housing 452. The first plate housing 452 defines first base housing key projections 454. The second plate assembly 434 comprises a second plate 460 and a second plate housing 462. The second plate housing 462 defines second base housing key projections 464 and extension housing key openings 466. The second plate 460 may be integrally formed with the base housing 462. The third plate assembly 436 comprises a third plate 470 and a plate housing 472. Extension housing key projections 474 are formed on the third plate housing 472.

The base plate 442 may be similar to the example base plate 42 described above. The second plate 460 may be similar to the example first plate 32 described above. The example first plate 450 may be similar to the second plate 34 described above. The example third plate 470 may be similar to the third plate 36 described above.

The fourth example phantom system 420 is configured to operate in first, second, third, and fourth configurations. In the first configuration, the base assembly 430 is used by itself to perform a chest image quality test.

In the second configuration, the first plate assembly 432 is detachably attached to the base assembly 430 using the base housing key openings 446 and the first base housing key projections 454. In this second configuration, the first plate assembly 432 and base assembly 430 are used to perform chest/skin dose test.

In the third configuration, the second plate assembly 434 is detachably attached to the base assembly 430 using the base housing key openings 446 and the second base housing key projections 464. The second plate assembly 434 and the base assembly 430 are used to perform an abdomen image quality test in the third configuration.

In the fourth configuration, the second plate assembly 434 is detachably attached to the base assembly 430 using the base housing key openings 446 and the second base housing key projections 464, and the third plate assembly 436 is detachably attached to the second insert base assembly 434 using the extension housing key openings 466 and the extension housing key projections 474. In this fourth configuration, the base assembly 430, the second insert assembly 434, and the third insert assembly 436 are used to perform an abdomen dose or doserate test.

It should be noted that the relative positions of the various projections and openings may be exchanged without affecting the fundamental operation of the fourth example phantom system 320 as described below.

Ideally, the base assembly 430, first plate assembly 432, second plate assembly 434, and third plate assembly 436 can all be sterilized (e.g., autoclaved) without damage.

VI. Example Test Environments

Figure 21A:
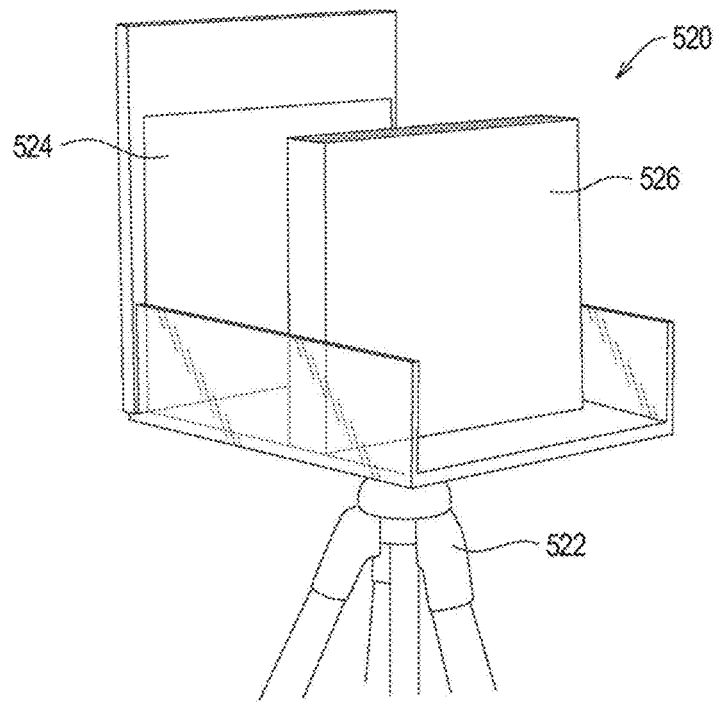
FIGS. 21A and 21B are perspective views illustrating the use of any of the example phantom systems described above in an image quality chest test configuration and a doserate chest test configuration.
Figure 21B:
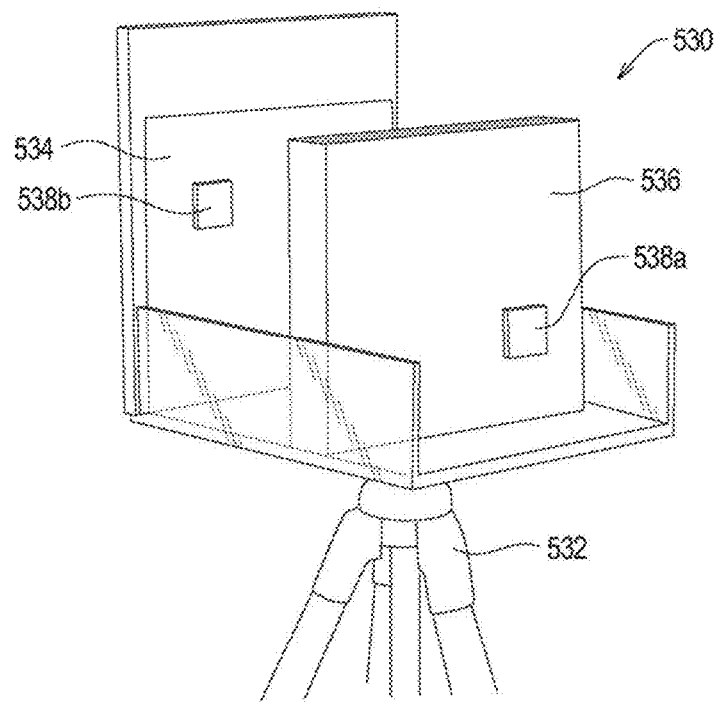
Figure 22A:
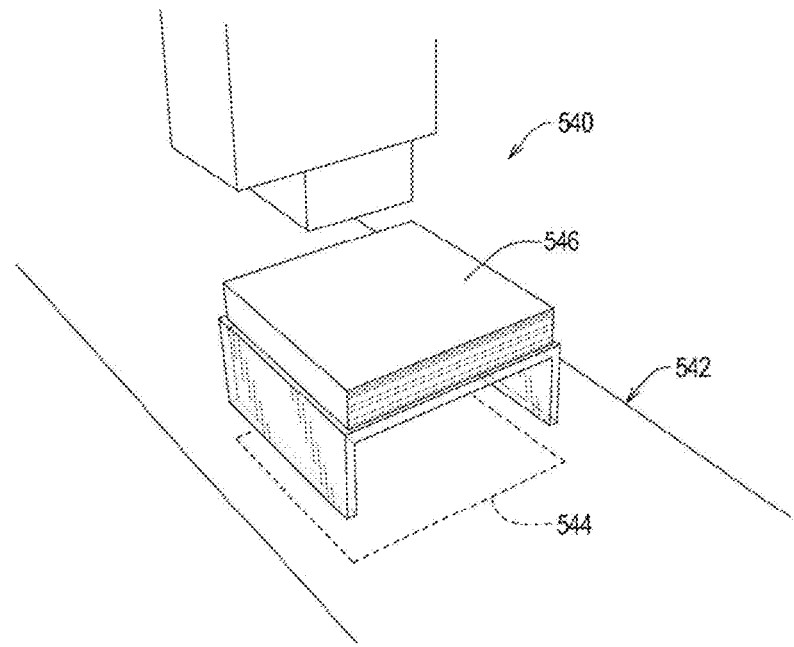
FIGS. 22A and 22B are perspective views illustrating the use of any of the example phantom systems described above in an image quality abdomen test configuration and a doserate abdomen test configuration.
Figure 22B:
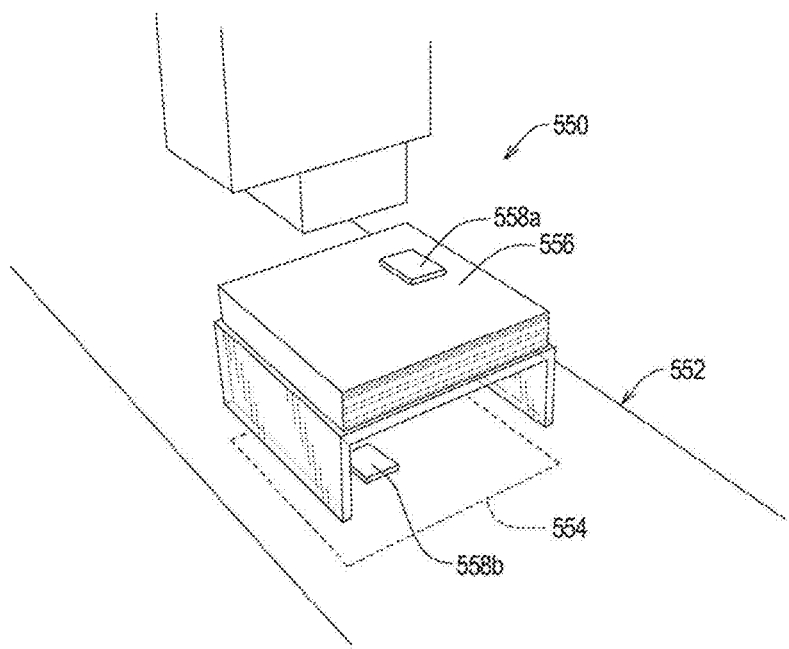

Most radiographic units can be used in two configurations: with a horizontal beam directed at a wall bucky for routine chest x-rays as shown in FIGS. 21A and 21B, and with a vertical beam directed at a table bucky for examinations of the abdomen of the supine or prone patient as shown in FIGS. 22A and 22B. Either configuration may be used ensepholometric (skull) imaging.

FIG. 21A depicts a first example use environment 520 in which a support structure 522 supports an x-ray image detection system 524 (e.g., film, computer radiography (CR), and digital radiography (DR)) and a phantom assembly 526 for use with a horizontal beam. FIG. 21B depicts a second example use environment 530 in which a support structure 532 supports an x-ray image detection system 534 (e.g., film, computer radiography (CR), and digital radiography (DR)) and a phantom assembly 536 for use with a horizontal beam. The second example use environment 530 further employs first and second dose detectors 538a (chest skin dose measurement detector) and 538b (imaging detector input dose detector) for measuring dosage on either side of the phantom assembly 536 in the direction of travel of the horizontal beam.

FIG. 22A depicts a third example use environment 540 in which a support structure or table 542 supports an x-ray image detection system 544 (e.g., film, computer radiography (CR), and digital radiography (DR)) and a phantom assembly 546 for use with a vertical beam. FIG. 22B depicts a fourth example use environment 550 in which a support structure 552 supports an x-ray image detection system 554 (e.g., film, computer radiography (CR), and digital radiography (DR)) and a phantom assembly 556 for use with a vertical beam. The fourth example use environment 550 further employs first and second dose detectors 558a (abdomen skin dose or doserate) and 558b (imaging detector input dose or doserate detector) for measuring dosage on either side of the phantom assembly 556 in the direction of travel of the vertical beam.

In both alignments, the same x-ray tube, energized by the same generator, may be employed. The amount of inherent and added filtration in the beam is fixed, but the kVp, mAs per exposure, and focal spot to detector distance are at the discretion of the operator.

The testing procedures for both radiographic and fluoroscopic units involve the use of a phantom assembly, together with the following additional equipment:

1 Any available commercial instrument capable of measuring exposure (in μSv), effective kVp and exposure time. Alternatively, separate instruments may be used to perform these functions;
2. An alignment test tool, incorporating radio-opaque indices to display field size and position on a film receptor;
3. A chest stand for chest exposures (FIG. 1) (incorporating a lead beam-defining plate);
4. A number of 1 or 2 mm thick 1100 aluminum plates with which to determine the HVL of the beam, and a number of Cu plates for uniformity and dosimetry assessments. An abdomen stand replaces the chest stand for abdomen-related tests with aluminum, copper and lead plates;
5. A radiation survey meter sensitive enough to measure scattered radiation;
6. A fluoroscopic RMI alignment test tool (or equivalent) used with copper plates and abdomen stand; and
7. Software for data entry, calculations and report generation.

Using a phantom system of the present invention and the additional equipment described in this Section VI, the following tests in radiography may be performed on x-ray generators according to standard testing protocols: Alignment Test; Kolovoltage kVp Test; Half Value Layer Test; Timer Accuracy and Reproducibility Test; Linearity Test; Wall Bucky Chest Image Quality Test; Patient Chest Dose Determination and Reproducibility Test; Radiation Survey near a chest unit; Table Bucky Abdomen Image Quality Test; Patient Abdomen Dose Determination and Reproducibility Test; Radiation Dose to Operator for Abdomen Protocol Test.

Similarly, the following tests in fluoroscopy may be performed using a phantom system of the present invention and the appropriate additional equipment as defined in this Section VI: Fluoroscopy Alignment Test; Fluoroscopy Image Quality; Patient Doserate in Fluoroscopy.

VII. Plate Material Selection

A description of the selection of materials and material dimensions of a phantom system constructed in accordance with the principles of the present invention will now be described.

1. Effect of the Variables Involved in X-Ray Generation

In this subsection, mAs correction factors for abdomen and chest examinations which make the air kerma emitted by the example phantom of the present invention equal that by the ACR phantom are determined.

First, the effect of the variables involved in x-ray generation, using the Spectrum abdomen (80 kVp) and chest (120 kVp) phantoms as models will be determined a compared to those involving the ACR phantom.

After measuring the Half-Value Layer (HVL) of the emitted beam, Reilly's method is used to determine the effective equivalent of aluminum in the x-ray beam as it emerges from the tube head. In the SR78 calculations, this amount of aluminum is added to that included in each phantom (ACR and Spectrum). Then, for four chosen HVL's at the two kVp's (80 ABD and 120 CHEST), the effective kVp, 1st HVL and Air Kerma in uGy/mAs are evaluated for the radiation emerging from the ACR and the example phantom of the present inventions. This allows for a comparison of the two in terms of the radiation transmitted by each.

The following Table 1 contains the results for the ACR Phantom for the following parameters: CHEST 120 kVp, 17 target, 0 ripple, 750 mm distance, 4.6 mm Al and 85.5 mm PMMA.

TABLE 1

| Measured HVL | Equivalent mm Al | Total Equiv Al | KeV | 1st HVL | uGy/mAs |
|---|---|---|---|---|---|
| 2.0 | 0.56 | 5.16 | 64.1 | 7.9 | 25.0 |
| 3.0 | 1.19 | 5.79 | 64.6 | 8.07 | 23.5 |
| 4.0 | 2.22 | 6.82 | 65.4 | 8.3 | 21.3 |

TABLE 1-continued

| Measured HVL | Equivalent mm Al | Total Equiv Al | KeV | 1st HVL | uGy/mAs |
|---|---|---|---|---|---|
| 4.5 | 2.86 | 7.46 | 65.0 | 8.5 | 20.0 |
| 5.0 | 3.59 | 8.19 | 66.3 | 8.65 | 18.8 |

The following Table 2 contains the results for an example phantom assembly constructed in accordance with the principles of the present invention under the following parameters: CHEST 120 kVp, 17 degree target, 0 ripple 750 mm distance example phantom of the present invention, including 9.5 mm PMMA, 12.7 mm Bone (the nearest equivalent to PVC), 12.48 water (equivalent to 12 mm ABS), No Al.).

TABLE 2

| Measured HVL | Equivalent mm Al | Total Equiv Al | KeV | 1st HVL | uGy/mAs |
|---|---|---|---|---|---|
| 2.0 | 0.56 | 0.56 | 65.3 | 8.44 | 66.9 |
| 3.0 | 1.19 | 1.19 | 65.7 | 8.6 | 63.2 |
| 4.0 | 2.22 | 2.22 | 66.3 | 8.78 | 57.7 |
| 4.5 | 2.86 | 2.86 | 66.3 | 8.9 | 54.6 |
| 5.0 | 3.59 | 3.59 | 67.0 | 9.0 | 51.3 |

The following Table 3 contains the results for the ACR Phantom under the following parameters: ABDOMEN 80 kVp, 17 target, 0 ripple, 750 mm distance; ACR phantom, including 4.6 mm Al and 202.5 mm PMMA.

TABLE 3

| Measured HVL | Equivalent mm Al | Total Equiv Al | KeV | 1st HVL | uGy/mAs |
|---|---|---|---|---|---|
| 2.0 | 1.44 | 6.04 | 55.3 | 7.0 | 0.353 |
| 3.0 | 3.03 | 7.63 | 55.9 | 7.2 | 0.299 |
| 4.0 | 5.19 | 9.79 | 56.7 | 7.48 | 0.241 |
| 4.5 | 6.54 | 11.14 | 57.1 | 7.6 | 0.212 |

The following Table 4 contains the results for an example phantom assembly constructed in accordance with the principles of the present invention under the following parameters: ABDOMEN: 80 kVp, 17 degree target, 0 ripple, 750 mm distance example phantom of the present invention 9.5 mm PMMA, 12.7 mm Bone, 6.0 mm Al, 18.72 mm water (equiv to 18 mm ABS).

TABLE 4

| Measured HVL | Equivalent mm Al | Total Equiv Al | KeV | 1st HVL | uGy/mAs |
|---|---|---|---|---|---|
| 2.0 | 1.44 | 7.44 | 55.6 | 7.2 | 7.95 |
| 3.0 | 3.03 | 9.03 | 56.2 | 7.4 | 6.78 |
| 4.0 | 5.19 | 11.19 | 56.8 | 7.6 | 5.5 |
| 4.5 | 6.54 | 12.54 | 57.2 | 7.7 | 4.83 |
| 5.0 | 8.14 | 12.74 | 57.5 | 7.8 | 0.182 |

Comparing the results in Tables 1 and 2, it can be seen that, while the emitted spectra are nearly identical, the kerma/mAs ratio of Spectrum/ACR is approx 2.7 at 120 kVp. Therefore, in practice, we divide the mAs used with the ACR phantom by this factor to arrive at the value of the mAs to be used with the example phantom of the present invention.

Comparing the results in Tables 3 and 4, the spectra are again nearly the same, while the kerma/mAs ratio Spectrum/ACR is approx 22 at 80 kVp. Therefore, in practice, we divide the mAs used with the ACR phantom by this factor to arrive at the value of the mAs to be used with the example phantom of the present invention. If it is considered desirable to adjust the kerma output of the example phantom of the present invention at both 120 and 80 kVp to equal that of the ACR phantom, additional absorption may be added. This is examined in the following subsection.

2. Determination of Thickness of Copper Plates Forming Example Second and Third Insert Plates In this subsection, the thickness of copper that will reduce the air kerma emitted by the example phantom of the present invention to equal that emitted by the ACR phantom, using the same mAs setting, will be determined.

Having, as a preliminary step, measured the HVL of the bare beam, Reilly's method is used to evaluate the effective equivalent of aluminum in it. In using SR78, we then add this amount of filtration to that provided by each phantom (ACR and Spectrum). Then, for four chosen HVL's at the two kVp's (80 ABD and 120 CHEST) we evaluate the effective kVp, 1st HVL and uGy/mAs, as follows:

From Tables 1 and 2 above, the following Table 5 may be obtained:

TABLE 5

| Row | Measured HVL | Equivalent mm Al | Total equiv Al | KeV eff | 1st HVL | uGy/mAs |
|---|---|---|---|---|---|---|
| 1 | 2.0 | 0.559 | 0.559 | 65.3 | 8.46 | 66.9 |
| 2 | | | +0.8 Cu | 76.5 | 11.5 | 22.0 |
| 3 | 3.0 | 1.19 | 1.19 | 65.7 | 8.59 | 63.2 |
| 4 | | | +0.8 Cu | 76.6 | 11.5 | 22.0 |
| 5 | 4.0 | 2.22 | 2.22 | 66.3 | 8.8 | 57.7 |
| 6 | | | +0.8 Cu | 76.9 | 11.6 | 20.7 |
| 7 | 5.0 | 3.59 | 3.59 | 67.1 | 9.05 | 51.3 |
| 8 | | | +0.8 Cu | 77.3 | 11.7 | 19.0 |

The figures in rows 2, 4, 6, and 8 demonstrate that when 0.8 mm of Cu is used as part of the example phantom of the present invention, the emergent Air Kerma is reduced to that emitted by the ACR phantom. The keV and HVL go up however.

Recalling Tables 3 and 4 above, the following Table 6 may be obtained:

TABLE 6

| Row | Measured HVL | Equiv mm Al | Total Equiv Al | KeV eff | 1st HVL | uGy/mAs |
|---|---|---|---|---|---|---|
| 1 | 2.0 | 1.44 | 7.44 | 55.7 | 7.22 | 7.78 |
| 2 | | | +2.1 Cu | 66.3 | 10.3 | 0.321 |
| 3 | 3.0 | 3.03 | 9.03 | 56.2 | 7.40 | 6.6 |
| 5 | | | +2.1 Cu | 66.4 | 10.5 | 0.288 |
| 5 | 4.0 | 5.19 | 11.19 | 56.5 | 7.62 | 5.35 |
| 6 | | | +2.1 Cu | 66.5 | 10.3 | 0.248 |
| 7 | 4.5 | 6.54 | 12.54 | 57.2 | 7.74 | 4.71 |

When 2.1 mm Cu is used as part of the abdominal example phantom of the present invention the emergent Air Kerma will be the same as that of the ACR phantom, as shown by the numbers in rows 3, 5, and 7.

3. X-Ray Mass Attenuation Coefficients

A) Bone and Polyvinyl Chloride

Figure 23:
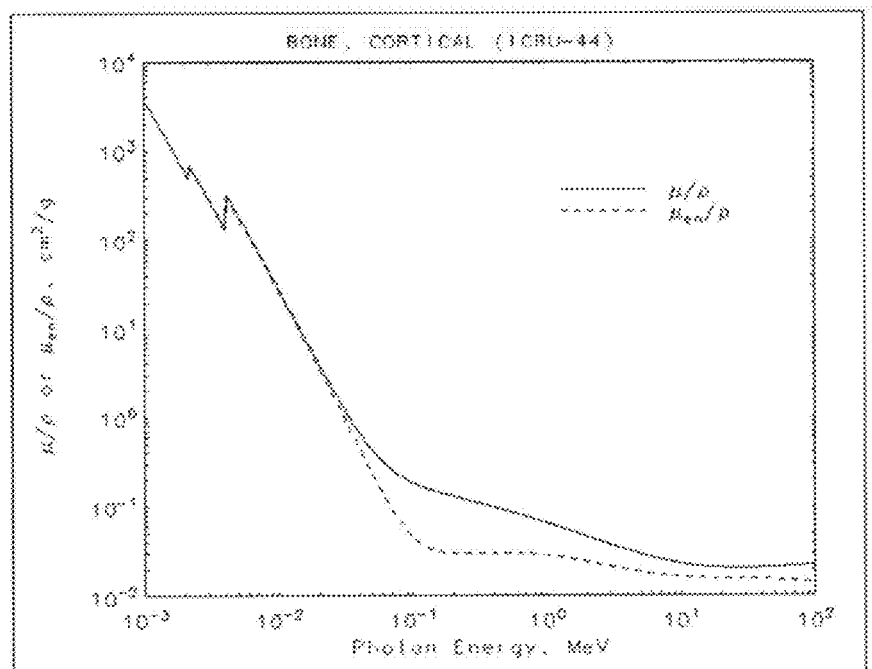
FIG. 23 is a first graph showing attenuation versus photon energy for bone.
Figure 24:
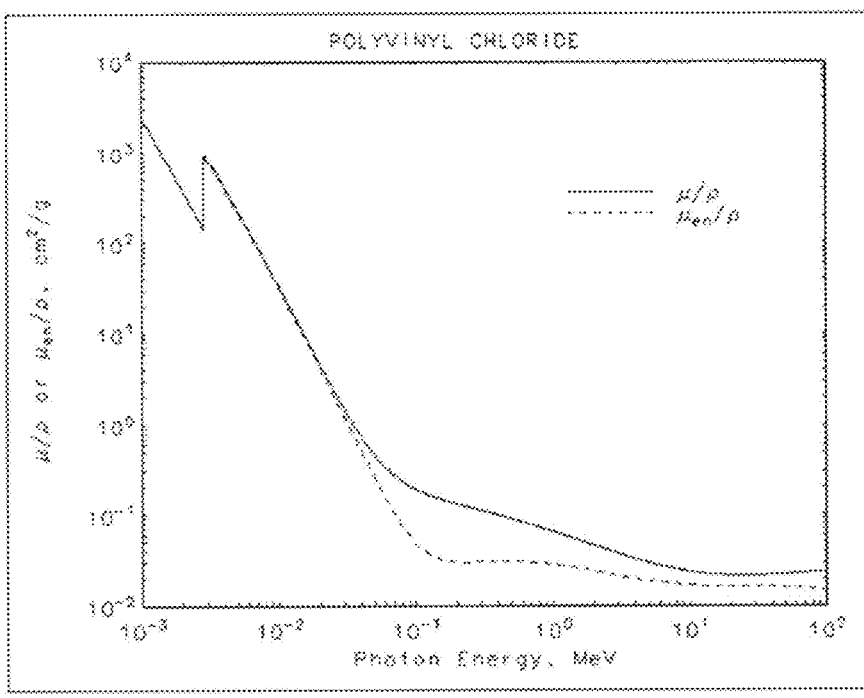
FIG. 24 is a second graph showing attenuation versus photon energy for PVC.

A comparison of FIGS. 23 and 24 shows attenuation versus photon energy in kV. The Applicant has determined that PVC is a close fit to the attenuation by bone and that PVC is an appropriate material that may be used as a replacement for or as a representative of bone in the phantom systems of the present invention.

B) Soft Tissue and PMMA

Figure 25:
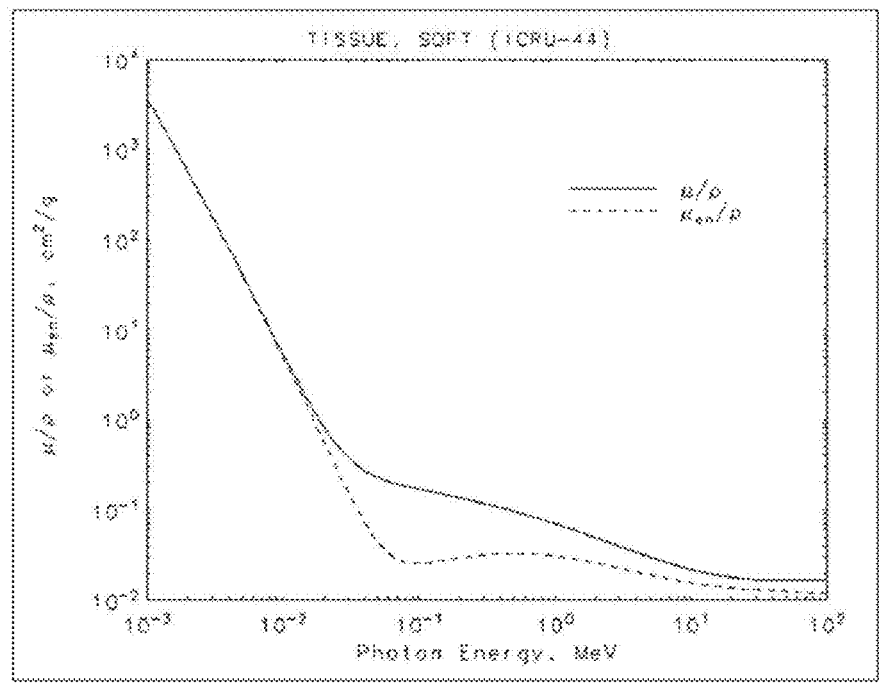
FIG. 25 is a third graph showing attenuation versus photon energy for soft tissue.
Figure 26:
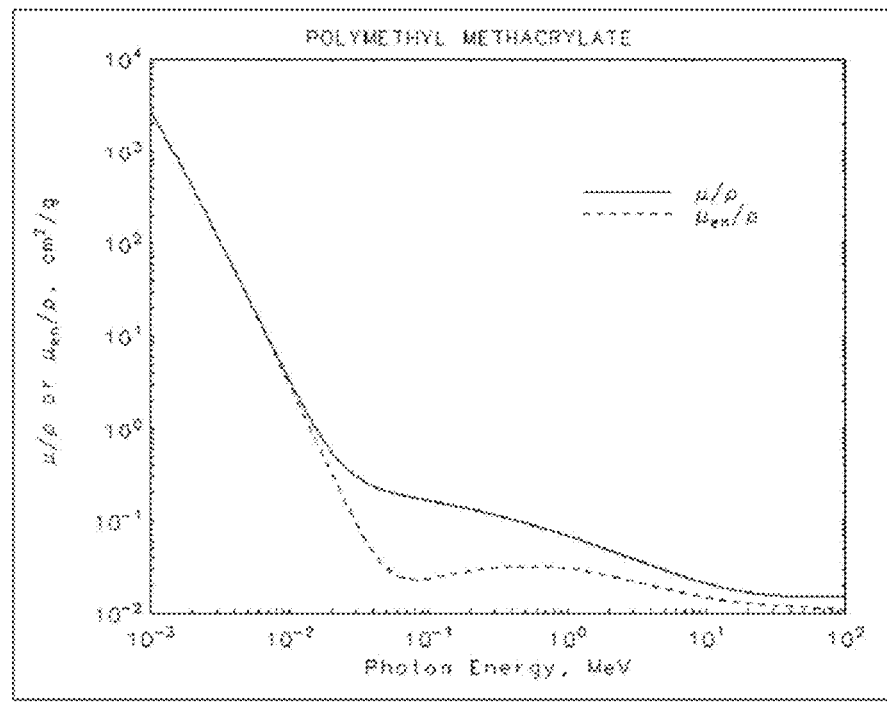
FIG. 26 is a fourth graph showing attenuation versus photon energy for PMMA.

As shown by a comparison of FIGS. 25 and 26, the Applicant has determined that the closest fit to attenuation by soft tissue is PMMA, so, correcting for density, PMMA is used as a tissue replacement in the example phantom of the present invention.

C) Material Constants and Composition Assumptions

The following Table 7 contains material constants and composition assumed in the present evaluations for compounds and mixtures. The compositions of various human tissues were taken from ICRU Report 44 (1989). Values are given for the mean ratio of atomic number-to-mass Z/A, the mean excitation energy I, and the density. Some density values are only nominal.

TABLE 7

X-Ray Mass Attenuation Coefficients

| Material | <Z/A> | I (eV) | Density (g/cm3) | Composition (Z: fraction by weight) | |
|---|---|---|---|---|---|
| Polymethyl Methacrylate | 0.53937 | 74.0 | 1.190 | 1: 0.080541<br>6: 0.599846 | 8: 0.319613 |
| Water, Liquid | 0.55508 | 75.0 | 1.000 | 1: 0.111898 | 8: 0.888102 |
| Polystyrene | 0.53768 | 68.7 | 1.060 | 1: 0.077421 | 6: 0.922579 |
| Polyvinyl Chloride | 0.51201 | 108.2 | 1.406 | 1: 0.048382<br>6: 0.384361 | 17: 0.567257 |
| Bone, Cortical (ICRU-44) | 0.51478 | 112.0 | 1.920 | 1: 0.034000<br>6: 0.155000<br>7: 0.042000<br>8: 0.435000<br>11: 0.001000 | 12: 0.002000<br>15: 0.103000<br>16: 0.003000<br>20: 0.225000 |

VIII. Third Example Image Plate

Figure 27:
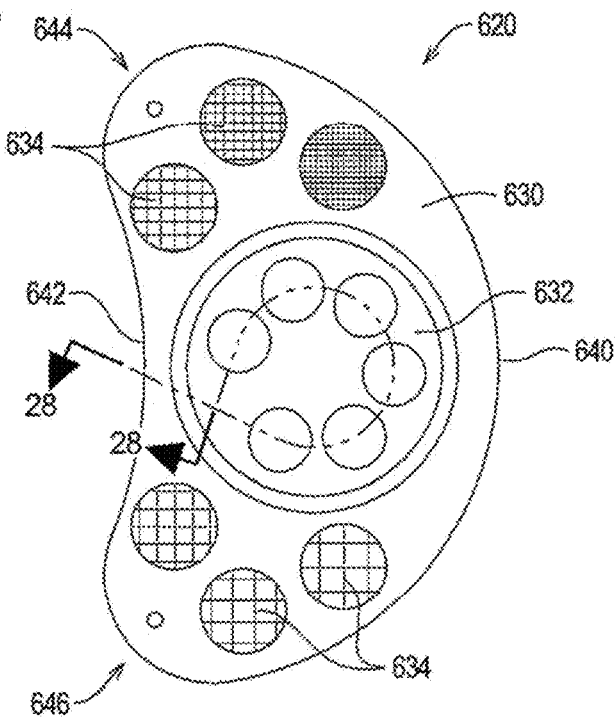
FIG. 27 is a plan view of a third example image plate of the present invention.
Figure 28:
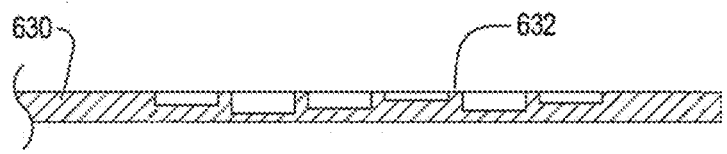
FIG. 28 is a section view taken along lines 28-28 in FIG. 27.
Figure 29:
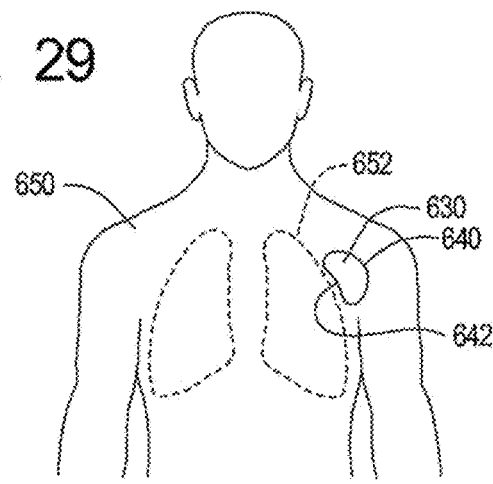
FIG. 29 is a front elevation view depicting the use of the third example image plate.

Referring now to FIGS. 27, 28, and 29, depicted therein is a third example image plate 620 constructed in accordance with, and embodying, the principles of the present invention. The third example image plate 620 comprises a plate body 630, an insert plate 632, and a plurality of mesh members 634. The plate body 630 is preferably made of PMMA, the mesh structures 634 are made of copper wire, and the insert plate 632 is preferably made of aluminum.

The example mesh structures 634 are 1.9 cm diameter copper mesh structures embedded in the PMMA slab at a depth of 5 mm that allow high contrast image resolution to be evaluated from images representing these structures 6344. The mesh structures are formed in a range of mesh sizes. As one example, the mesh structures may range in size from 0.5 lp/mm to 3.2 lp/mm in nine steps. In the example image plate 42, the wires in the mesh structures are aligned at 45° to the cathode/anode direction.

Low contrast resolution may be evaluated from the images of six holes in the insert plate 632. In the example image plate 42, the holes have depths in the range of 0.1 mm to 1.7 mm and are randomly distributed along a circular line.

As shown in FIGS. 27 and 29, the plate body 630 defines a convex curved edge 640 and a concave curved edge 642 joined by end portions 644 and 646. The example plate body 630 is arranged on or near to a patient 650 such that the concave curved edge 642 avoids a lung location 652 of the patient. The plate body 630 is left in place during an x-ray process in which an image is made of the patient's lungs. The image formed by the plate 620 is thus associated with the patient and can be subsequently used to verify the accuracy of the image of the patient's lungs.

IX. Sixth Example Phantom System

Referring now to FIGS. 30-44, depicted therein is a sixth example test phantom 720 constructed in accordance with, and embodying, the principles of the present invention. The sixth example test phantom 720 is configured for use with intraoral dental x-ray units and will also be referred herein to as a dental test phantom 720.

The example dental test phantom 720 comprises first, second, and third contrast steps 722a, 722b, and 722c, an image plate 724, first and second lead inserts 726a and 726b, and first and second mesh inserts 728a and 728b. The example dental test phantom 720 further comprises a mounting assembly 730 for supporting the contrast steps 722, image plate 724, lead inserts 726, and mesh inserts 728 in a desired spatial relationship during use. The example mounting assembly 730 comprises a base member 732, first and second spacing rings 734a and 734b, first, second, and third leg members 736a, 736b, and 736c, a cover plate 738, and film holder 740, and a sensor holder 742. The contrast steps 722a, 722b, and 722c are formed as cavities in the base member 732 to define difference thicknesses of the base member 732 along a measurement axis A along which the x-rays travel during use of the example dental test phantom 720 as will be described in further detail below.

In use, the example dental test phantom 720 is used to assess image quality produced by intraoral dental X-ray units employing either film or digital detectors. The example dental test phantom 720 is simple to position vis-à-vis the x-ray unit, and the information produced is easily interpreted.

The example dental test phantom 720 may be used during the acceptance and routine testing of dental X-ray equipment, for the periodic quality control of the whole imaging process, and during system optimization. The example dental test phantom 720 allows direct comparison of the results obtained from different dental units and using different imaging systems. Image quality information obtained using the example dental test phantom 720 may be used with film and/or digital dental X-ray equipment.

The example dental test phantom 720 is designed to be used with normal bitewing exposures between 60 and 90 kVp. Accordingly, the routine settings on the X-ray unit under examination are used during testing with the example dental test phantom 720. A single standard bitewing exposure of the phantom is all that is required to produce each quality assessment image. From this exposure of the film (or digital sensor), density, contrast, scatter to primary ratio, limiting resolution, and an estimate of image fog or background may be evaluated using the example dental test phantom 720.

The example film holder 740 is adapted to support film, and the example sensor holder 742 is adapted to support a digital sensor. The exact construction (e.g., shape, size, and/or dimensions) of the film holders 740 and 742 can be designed to accommodate one or more sizes of film and one or more sizes of digital sensors such as digital type 1 sensors used for children and/or digital type 2 sensors used for adults.

The example image plate 724 is made of aluminum, and digital images of the aluminum image plate are analyzed for tooth resolution at different contrasts in aluminum, in different PMMA contrast based on the spatial locations of the steps 722a, 722b, and 722c, and combinations of the spatial orientations of the PMMA contrast steps 722 and the aluminum materials forming the image plate 724. The following discussion contains suggestions for the assessment of subjective parts of an image (i.e. limiting resolution and film artifacts).

The example phantom 720 is a self-contained unit but uses the example film holder 740 to hold film (including PSP) and the example sensor holder 742 for wired digital detectors. The example sensor holder 742 may be provided for type 1 and type 2 sensors, in which case a total of one film holder 740 and two sensor holders 742 are supplied.

Figure 32:
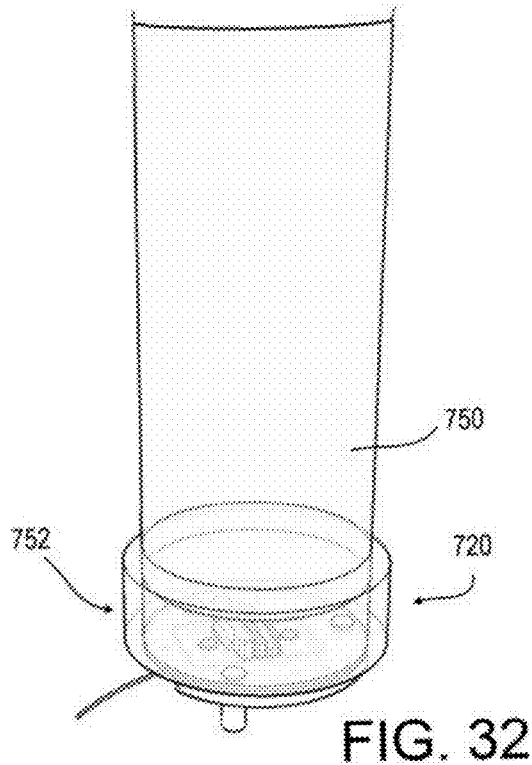
FIG. 32 is a perspective view of the example dental test phantom operatively connected to an intraoral dental x-ray system.

Optionally, a separate phantom stand (not shown) may be used to facilitate the testing but is not needed. An optional collimator alignment tool (not shown) adapted to help positioning may be used but is also not required in most situations in which with step wedges 722 are used instead of holes. An optional alignment tool (not shown) may be used to attach the phantom to the collimator independently of the position of the x-ray 750 as shown in FIG. 32. The example phantom 720 is typically supplied in a protective plastic storage box (not shown) with a magnifying glass (not shown), user manual, and examples of tables of results. The protocols for using the phantom will now be described in further detail below.

A 76.5 mm diameter by 46.3 mm thick PMMA #4 cylinder weighing about 350 g is used to form the base member 732 of the example dental test phantom 720. The overall thickness of the example phantom 720 is chosen to produce an optimum density range at the detector and to simulate the normal X-ray attenuation and spectra of a bitewing X-ray exposure. Separate holders 740 for film and PSP and 742 for digital detectors are provided to allow the appropriate film or sensor to be attached to the example dental test phantom 720.

Referring now to FIGS. 33A-H, the use of the example phantom 720 with a digital sensor 752 and the example X-ray tube 750 of an X-ray system under test will be described. The sensor holder 742 holds the sensor 752 in place relative to the phantom 720 as shown, for example, in FIG. 33B.

Figure 30A:
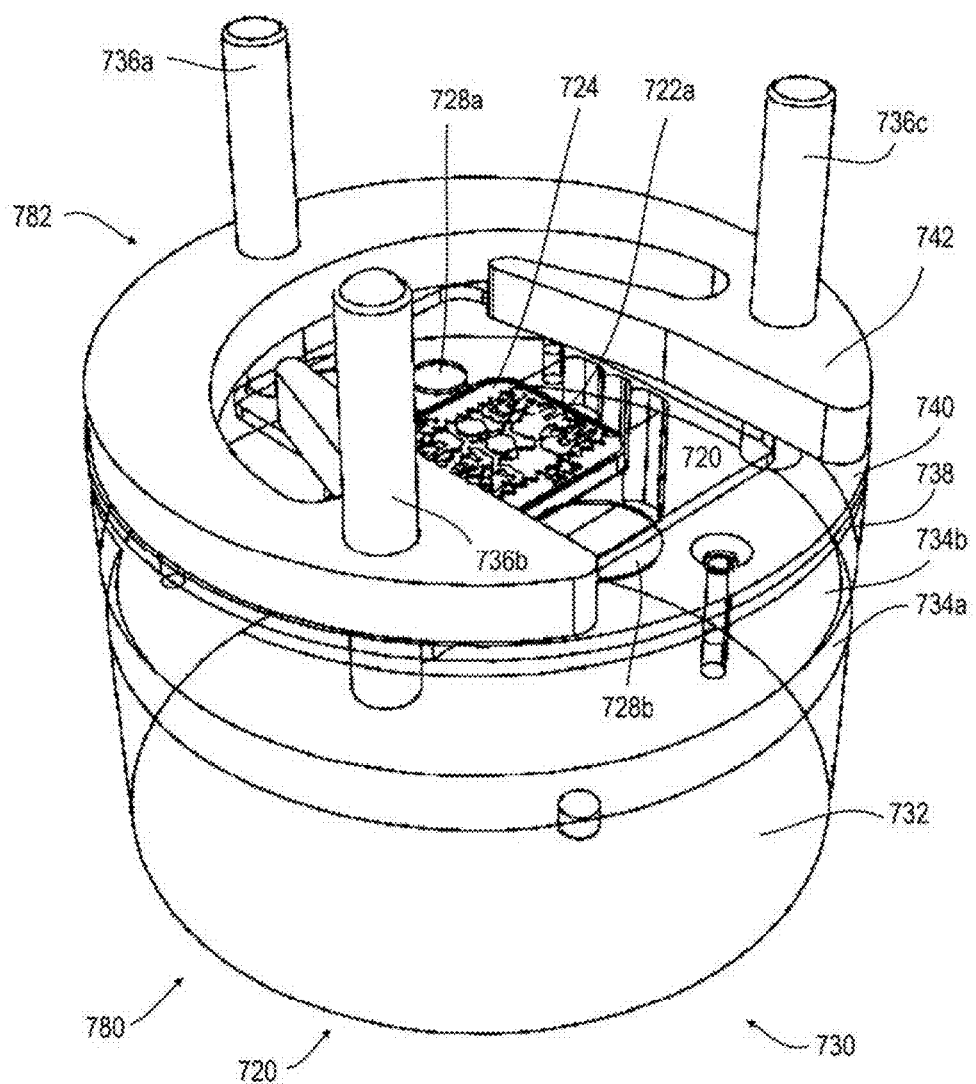
FIGS. 30A and 30B are perspective and exploded views, respectively, of an example dental test phantom of the present invention for adapted for use with intraoral dental x-ray systems.
Figure 30B:
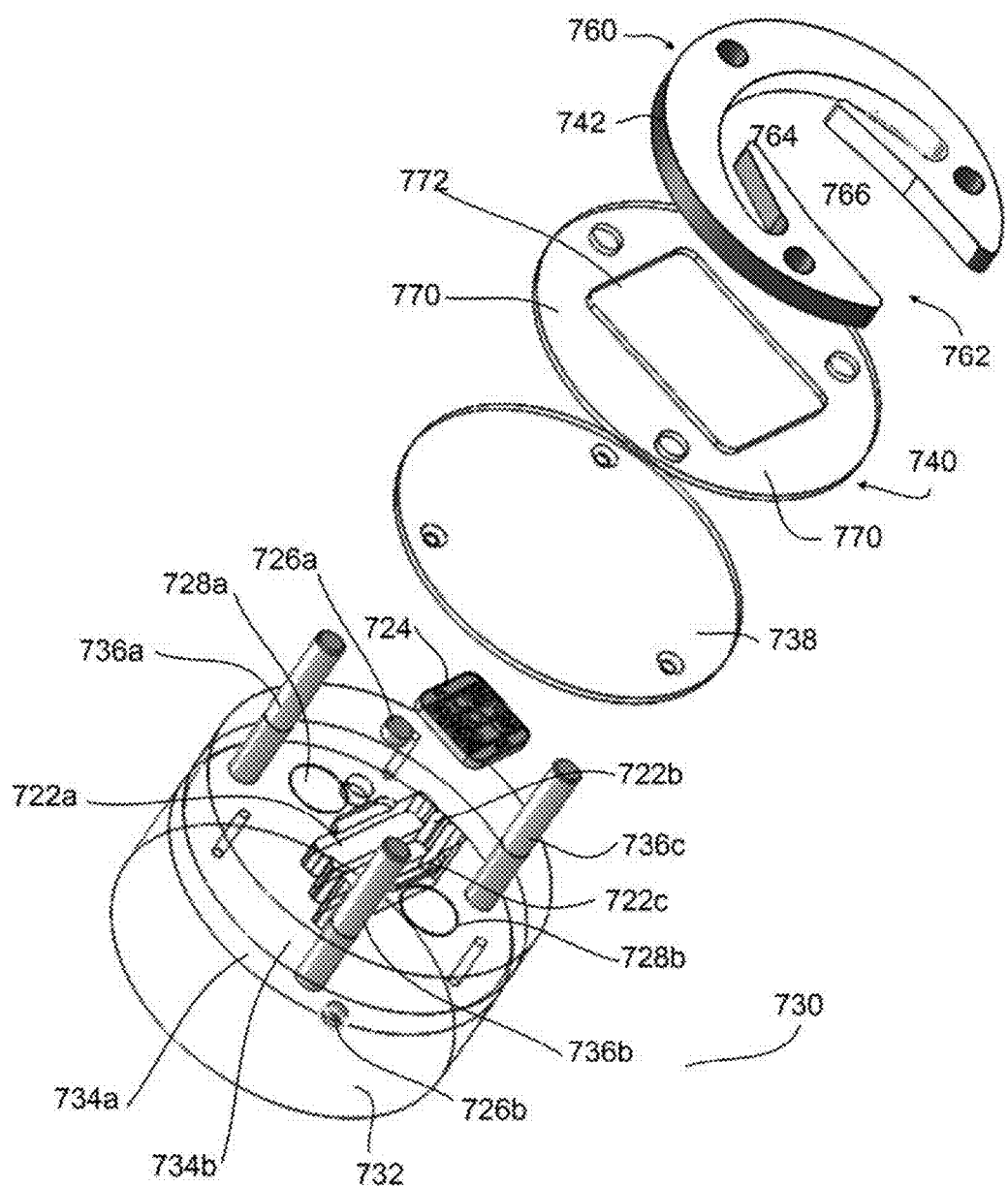
Figure 31:
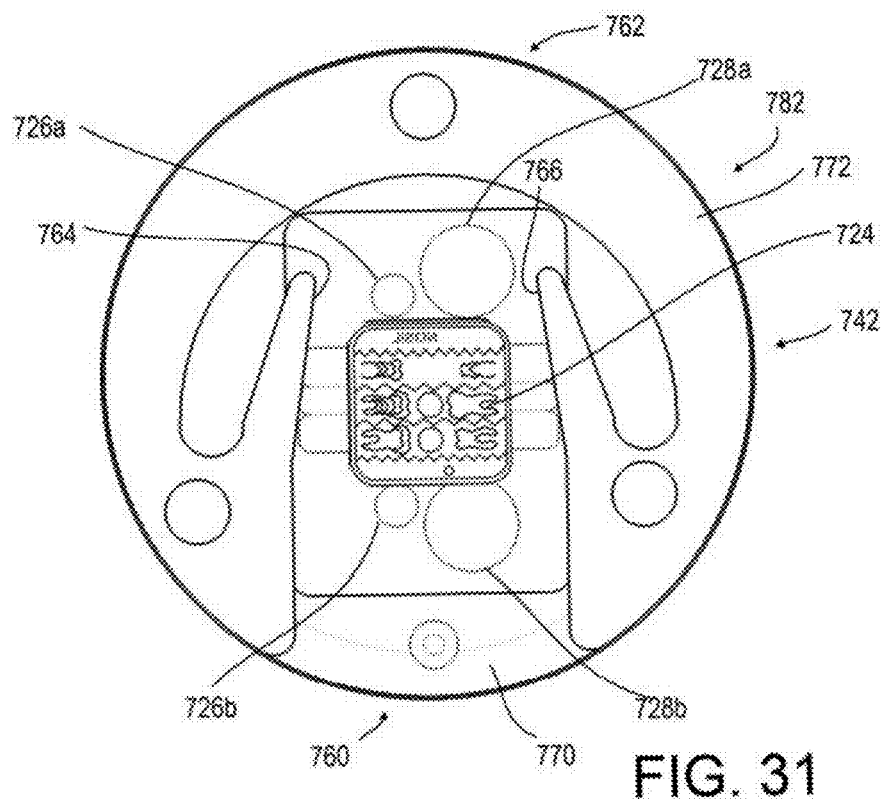
FIG. 31 is a plan view of a receiving end of the example dental test phantom of FIGS. 30A and 30B.

In particular, as perhaps best shown in FIGS. 30A, 30B, and 31, the sensor holder 742 is a generally circular member defining a closed end 760, an open end 762, and first and second engaging portions 764 and 766. The sensor 752 is slid through the open end 762 and between the first and second engaging portions 764 and 766. The sensor holder 742 is made of a resiliently deformable material such as plastic, and the distance between the engaging portions 764 and 766 is slightly smaller than the sensor 752. Accordingly, when the sensor 752 is inserted between the engaging portions 764 and 766, the engaging portions 764 and 766 apply pressure on the sensor 752 to maintain the sensor in a desired spatial relationship with the remaining components of the example phantom 720.

The example sensor holder 740 is a generally circular plate 770 defining a film cavity 772 for supporting film. The example film cavity 772 is rectangular to fit standard X-ray imaging film for use in dental X-ray systems. The sensor holder 742 is typically used with the film holder 740 to hold the film in the film cavity 772 during use of the example phantom 720, especially when the phantom 720 is inverted.

As generally depicted in FIGS. 30A, 30B, and 31, one or more embedded structures, such as contrast steps 722, the image plate 724, lead inserts 726, and mesh inserts 728 are supported by the mounting assembly 730. These embedded structures, alone or in any combination, allow a range of tests to be performed as generally described above with respect to the first through fifth example phantom assemblies and as will be described in further detail below.

Referring again to FIGS. 30A, 30B, and 31, x-rays are transmitted along the transmission axis A through the example dental test phantom 720 from a source end 780 to a receiving end 782.

Densities measured on the film receptor (D) or gray scale/pixel density measured on the digital receptor (G) are produced by x-rays transmitted through the example dental test phantom 720. To produce a meaningful measurement of the various densities relevant to proper operation of a intraoral x-ray system, the example dental test phantom 720 comprises the first, second, and third contrast steps 722*a*, 722*b*, and 722*c*, an image plate 724, first and second lead inserts 726*a* and 726*b*, and first and second mesh inserts 728*a* and 728*b* as will be described in further detail below.

The contrast steps 722*a*, 722*b*, and 722*c* are formed in the PMMA base member 732 and are separated and risers of 5.8 mm air (40.5 PMMA), 9.8 mm air (36.5 PMMA), 13.8 mm air (32.4 PMMA), respectively. The number of contrast steps and dimensions thereof are provided as examples only, and different numbers and dimensions of the contrast steps 722 may be used as preferred for a particular test protocol. In the example dental test phantom 720, three aluminum inserts 724*a*, 724*b*, and 724*c* defined by the image plate 724 are in line with the contrast steps in the PMMA as perhaps best shown in FIG. 31. Each aluminum insert 724*a*, 724*b*, and 724*c* each define two tooth images for a total of six total tooth images. The example inserts 724*a*, 724*b*, and 724*c* define thicknesses of 0.4, 0.5 and 0.9 mm, respectively. A seventh density reading is for the total thickness of PMMA at a location outside of the contrast steps 722. The first and second lead inserts 726*a* and 726*b* are circular plates of different diameters to provide Resolution is assessed using two copper mesh inserts 728*a* and 728*b* of 150 and 200 mesh, respectively, where the mesh values are specified in line pairs per inch.

The following Table A summarizes the different densities measured using the example dental test phantom 720:

TABLE A

| Density Measurement | Measured Structure | Comments |
|---|---|---|
| 1 | Step 5.8 mm air + 40.5 mm PMMA | D or G (5.8 mm air) |
| 2 | Step 9.8 mm air + 36.5 mm PMMA | D or G (9.8 mm air) |
| 3 | Step 13.9 mm air + 32.4 mm PMMA | D or G (13.9 mm air) |
| 4 | 46.0 mm PMMA + 3 mm plate Pb | D or G (PMMA, Pb at detector) |
| 5 | 46.0 mm PMMA + 3 mm plate lead | D or G (PMMA, Pb at collimator) |
| 6 | Six Al teeth (0.4, 0.5 and 0.9 mm Al) | D or G (tooth1, tooth2 . . . tooth6) |
| 7 | 46.3 mm PMMA | D or G (Background) |
| 8 | Resolution mesh 1 | R (5.906 lp/mm) |
| 9 | Resolution mesh 2 | R (7.874 lp/mm) |

The following Table B illustrates resolution measurements and the results of the analysis of such measurements.

TABLE B

| Mesh lp/inch | 100 | 120 | 150 | 200 | 325 | 400 |
|---|---|---|---|---|---|---|
| Mesh lp/mm | 3.947 | 4.724 | 5.906 | 7.874 | 12.795 | 15.748 |
| Result | Fail | Poor | Fair | Good | Perfect | Excellent |

In general, contrast at different values as measured above is compared with standard values. Standard values used for a baseline in such comparisons include reference levels (RL) and achievable levels (AL). RL and AL values are used as a comparison to yield a pass or fail for each measurement. Similar, values associated with resolution, scatter to primary ratio, maximum gray levels, and minimum gray levels are all compared to RL and AL values for a pass/fail determination. The RL and AL values are established by publicly available National Council on Radiation Protection & Measurements (NCRP) definitions.

Referring now to FIG. 32 of the drawing, depicted therein is the example dental test phantom 720 with the example X-ray tube 750 positioned on the source end 780 (top end in FIG. 32) and the digital image sensor 752 secured at the receiving end 782 (bottom end in FIG. 32). Although FIG. 32 illustrates the example dental test phantom 720 in use with circular collimator and a digital image sensor 752, the example dental test phantom 720 is designed for use with intraoral X-rays units having circular or rectangular collimators and which use D, E or F films, photo stimulated phosphor (PSP) plates, or digital detectors.

Figure 33A:
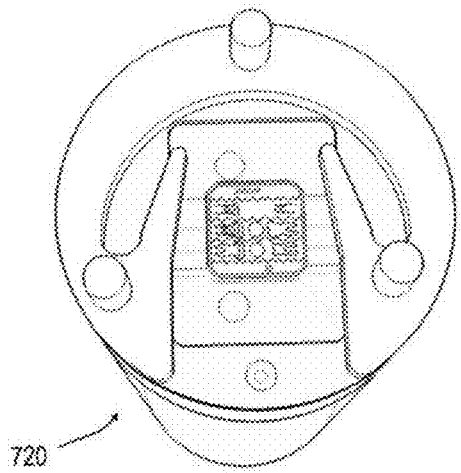
FIGS. 33A-33H illustrate the process of operatively connecting the example dental test phantom to an intraoral dental x-ray system for use in a vertical configuration.
Figure 33B:
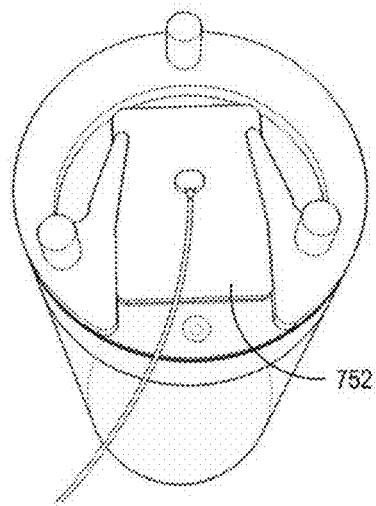

The positioning the example dental test phantom 720 with respect to the x-ray tube 750 and detector 752 will now be described in detail with respect to FIGS. 33A-33H. The receiving end 782 of the example dental test phantom 720 is illustrated in an inverted position and without a receiving unit in FIG. 33A. FIG. 33B illustrates that, with the example phantom 720 so inverted, the digital detector 752 is inserted into the open end 762 and between the engaging portions 764 and 766 of the sensor holder 742 such that the digital detector 752 is secured in a desired relationship to the remaining components of the example dental test phantom 720. Alternatively, a bitewing X-ray film (enclosed in #2 holder, its packet size—32×42 mm) may be slid into the film cavity 772 and under the sensor holder 742. In either case, the positioning is easily reproducible without the need of identifying marks or ancillary equipment.

Figure 33C:
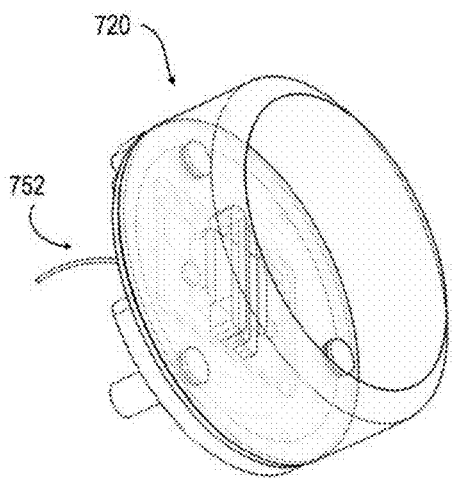
Figure 33D:
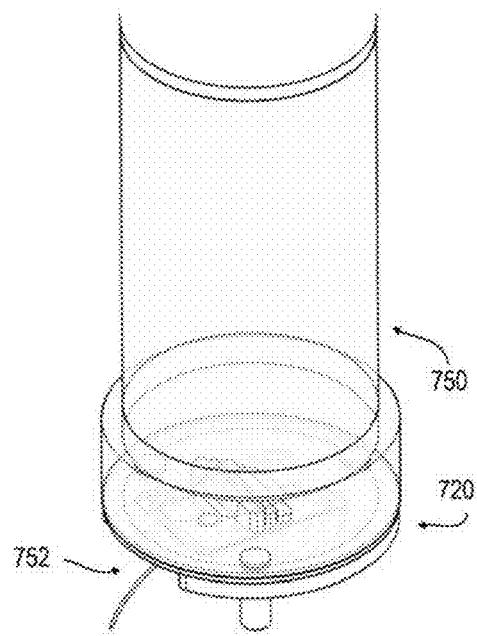
Figure 33E:
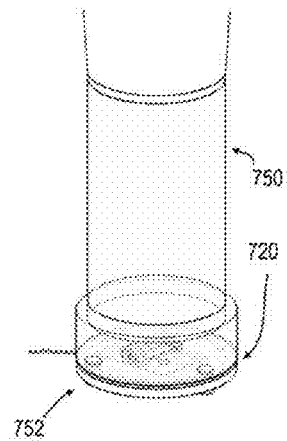
Figure 33F:
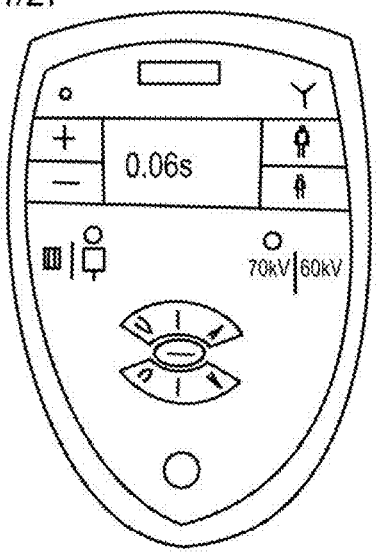
Figure 33G:
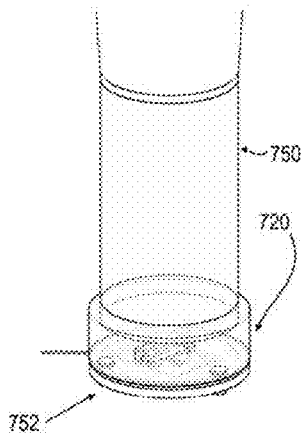
Figure 33H:
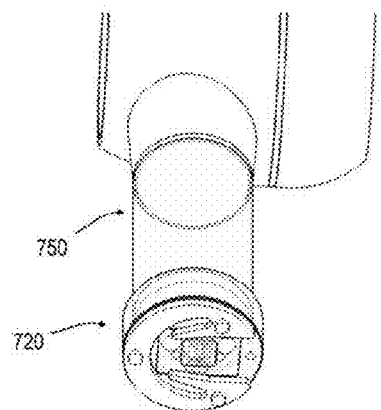

Referring now to FIG. 33C, the dental test phantom 720 is flipped over and then placed on a work surface with the source end facing up. At this point, the x-ray tube 750 is lowered towards the work surface until the x-ray tube 750 engages with the base member 732 of the example phantom 720 such that the x-rays propagate along the measurement axis A. The x-ray system is then operated as shown in FIG. 33E using bitewing parameters as shown, for example, in FIG. 33F to cause the detector (e.g., sensor 752) to be exposed to x-rays that have passed through the example phantom 720. After the exposure is complete as shown in FIG. 33G, the detector, in this case the sensor 752, is removed from the example phantom 720.

Figure 34A:
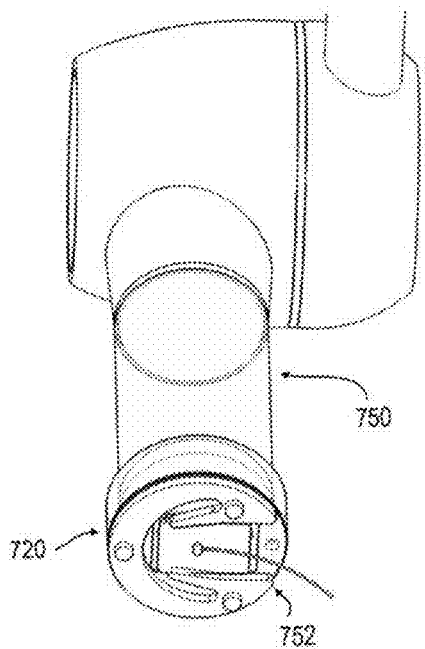
FIGS. 34A-C illustrate the process of operatively connecting the example dental test phantom to an intraoral dental x-ray system for use in a horizontal configuration.
Figure 34B:
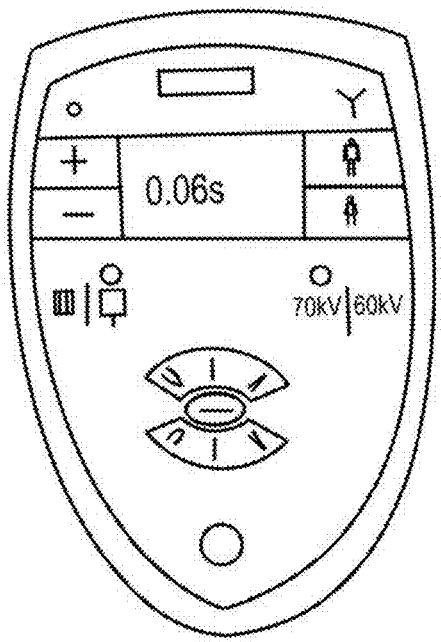
Figure 34C:
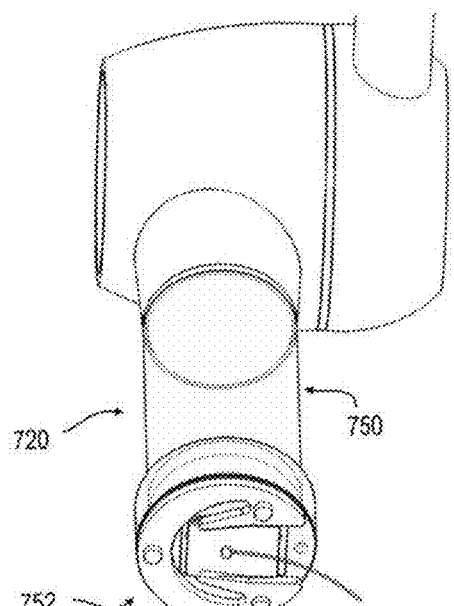

FIGS. 34A-34C illustrate the use of the phantom 720 in a horizontal configuration.

The data collected by the detector, in this case the sensor 752, is then analyzed for density and resolution variances from acceptable parameters associated with the example dental test phantom 720. In the case of digital data, the analysis may be performed by comparing an image on a screen with a test image or programmatically using test software. In the case of film, the analysis can be performed manually with the assistance of a magnifying glass or the like. For both types of detectors, the seventh density reading is for the total thickness of PMMA.

In particular, if the detector is film, once the film is exposed and developed, the following measurements can be made using a densitometer and a magnifying glass:
1. D1: Step 5.8 mm air+40.5 mm PMMA.
2. D2: Step 9.8 mm air+36.5 mm PMMA.
3. D3: Step 13.9 mm air+32.4 mm PMMA.
4. D4: 46.0 mm PMMA+3 mm plate Pb, (with the Pb next to the detector).
    The measured density is that of base plus fog.
5. D5: 0.3 mm plate lead+46.0 mm PMMA, (with the lead on the entrance surface). The measured density is that of pure scatter from the surround plus base plus fog, with no contribution from the primary radiation.
6. D6: Six Al teeth (0.4, 0.5 and 0.9 mm Al). Mark visible tooth elements.
7. D7: 46.3 mm PMMA primary plus scatter plus base plus fog.
8. R1: Resolution mesh 1 at 5.906 lp/mm (150 lp/inch).
9. R2: Resolution mesh 2 at 7.874 lp/mm (200 lp/inch).

When the detector is a digital sensor such as the sensor 752, the following measurements are made using data visualization on a computer display and/or automated visual data comparison software:
1. G1: Step 5.8 mm air+40.5 mm PMMA.
2. G2: Step 9.8 mm air+36.5 mm PMMA.
3. G3: Step 13.9 mm air+32.4 mm PMMA.
4. G4: 46.0 mm PMMA+3 mm plate Pb, (with the Pb next to the detector).
    The measured gray scale level is that of base plus fog.
5. G5: 0.3 mm plate lead+46.0 mm PMMA, (with the lead on the entrance surface). The measured gray scale level is that of pure scatter from the surrounding plus base plus fog, with no contribution from the primary radiation.
6. G6: Six Al teeth (0.4, 0.5 and 0.9 mm Al). Mark visible tooth elements.
7. G7: 46.3 mm PMMA primary plus scatter plus noise.
8. R1: Resolution mesh 1 at 5.906 lp/mm (150 lp/inch).
9. R2: Resolution mesh 2 at 7.874 lp/mm (200 lp/inch).

In particular, computer-displayed images of the nine test areas are examined by a suitable computer program which determines the bit level (0-256) of the pixels in a 4×4 mm area, or other selected area of the image, and averages them. These gray level data can then be interpreted in a similar way as density values to those derived for film.

Spatial resolution is determined from visual and computer-scanned examination of the images of the 2 copper mesh graticules in two orthogonal directions, using a magnifying glass for film or other image processing for digital image.

A label as shown in FIG. 35 may be used on the example dental test phantom 720. While tube axis, position of the focal spot and anode, is not critical, the label helps with consistency of positioning. The "A" and "C" indicia are arranged such that they are below the Anode and Cathode sides, respectively, of the x-ray tube 750. In this way, Hill effect is always the same and the phantom 720 can be used in the same configuration during each test.

From the measurements discussed above, the following parameters can be calculated to yield conclusions about the specific x-ray system under test.

For Film:

| Parameter | Summary of Calcuation |
| --- | --- |
| Contrast scale | Maximum range given by D3/D7 |
| Contrast between steps | Comparison between D3, D2, D1, and D7 |
| Tooth to background | Given by the ratio D6/D7 contrast |
| Limiting Resolution | The finest mesh that can be seen in both orthogonal directions |

-continued

| Parameter | Summary of Calcuation |
|---|---|
| Appropriateness of the technique factors used | D7 should be close to 1.5 |
| Scatter to primary ratio | given by (D5 − D4)/(D7 − D5) |

For Digital Sensors (Example of Calculation Appendix)

| Parameter | Summary of Calcuation |
|---|---|
| Contrast scale | Maximum range given by G3/G7 |
| Contrast between steps | Comparison between G3, G2, G1, and G7 |
| Tooth to background contrast | Given by the ratio G6/G7 |
| lp/mm Limiting Resolution | The finest mesh that can be seen in both orthogonal directions |
| Appropriateness of the technique factors used | G7 should be constantly |
| Scatter to primary ratio | given by (G5 − G4)/(G7 − G5) |
| Maximum Gray Level (Ideal) | 256 |
| Minimum Gray Level (Ideal) | 0 |

The example protocol described above can be used with all dental units and may be varied as necessary. The angular orientation of the x-ray beam is immaterial.

The example phantom 720 may be useful as a departmental quality assurance system where it can be employed to check techniques, the optimal operation of the X-ray units, and film processing.

The foregoing description of the example dental test phantom 720 describes a certain test protocol but takes no position on the results of the tests or how to interpret them. The visual judging of the limiting spatial resolution and the number of discernible lines is subjective and may require training and experience.

X. Collimation Device Mounted Examples

Referring now to FIG. 45, depicted at 820 therein is yet another example test phantom constructed in accordance with, and embodying, the principles of the present invention. The example test phantom 820 comprises an absorption portion 822 and an image plate portion 824. The example test phantom 820 is shown being used with a support surface (e.g., table) 830 and an x-ray system comprising a collimation device 832 and a detector 834. The absorption portion 822 is mounted onto the collimation device 832 and the image plate portion 824 is arranged on the support surface 830. X-rays propagating from the collimation device 832 to the detector 834 pass through the absorption portion 822 and the image plate 824. The example absorption portion 822 is reconfigurable (e.g., multiple plates) as described above to obtain different test results. The absorption portion 822 is further sized, dimensioned, and configured to be supported by standard attachment systems forming a part of the collimation device 832.

Depicted at 850 in FIG. 46 is yet another example test phantom constructed in accordance with, and embodying, the principles of the present invention. The example test phantom 850 comprises an absorption portion 852 and an image plate portion 854. The example test phantom 850 is shown being used with a support surface (e.g., table) 860 and an x-ray system comprising a collimation device 862 and a detector 864. The absorption portion 852 and image plate portion 854 are mounted onto the collimation device 862 such that x-rays propagating from the collimation device 862 to the detector 864 pass through the absorption portion 852 and the image plate 854. The example absorption portion 852 is reconfigurable (e.g., multiple plates) as described above to obtain different test results. The absorption portion 852 and image plate 854 are further sized, dimensioned, and configured to be supported by standard attachment systems forming a part of the collimation device 862.

With reference to the example test phantoms 820 and 850 described above, the absorption plate or plates forming the absorption portions 822 and 852 and the image plates 824 and 854 may be placed on the support surface 830 or 860, inside the collimation device 832 or 862, or at any location between the collimation device 832 or 862 and the detector 834 or 864, respectively. In addition, any of the example test phantoms described herein could be built into the x-ray system (e.g., into either the collimation device 832, 862 or the detector 834,864) in a way that the test phantom can be rotated into the path of the radiation for calibration and testing and out of the path of the radiation for diagnostic use.

XI. Additional Considerations

Some criteria for 'pass' and 'fail' used arise from the results of the NEXT (Nationwide Examination of X-ray Trends) of the FDA in the USA. In this program, the performance of a large number of medical and dental x-ray units was examined over a period of years. It was found that, while the values of significant measured parameters (e.g., Entrance Skin Exposure, Half Value Layer, High and Low Contrast Range, and Detail Resolution) varied widely, most units produced values close to a median for each parameter. A unit, which produces values differing widely from the median, is considered to have 'failed', and a recommendation is made for corrective measures. As an alternative to the NEXT standards, NCRP Report No. 172 defines Diagnostic Reference Level DRL and Diagnostic Achievable level DRA.

In short, if, in examining a unit, a parameter has been measured and the result found to be widely divergent from the NEXT median value, that measurement is reported as a 'failure', and a recommendation is made that the unit be serviced in order to bring it into the acceptable range.

Referring now to FIGS. 36-42, the analysis of various test images will be described.

FIG. 36 illustrates a situation in which gray level air steps are low. In this case, the aluminum image plate width is 18.9 mm, total measured width in 762 pixels. Calibration factor is 0.0248 pixel/mm; average gray level on G7/G3/G2/G1/G7 is 35/0/8/18/35.

In FIG. 37, gray levels air steps for bitewing exposure are depicted. In this case, an aluminum image plate width is 18.9 mm, total measured width in 762 pixels. Calibration factor is 0.0248 pixel/mm, average gray level on G7/G3/G2/G1/G7 is 30/0/5/15/30.

Figure 38:
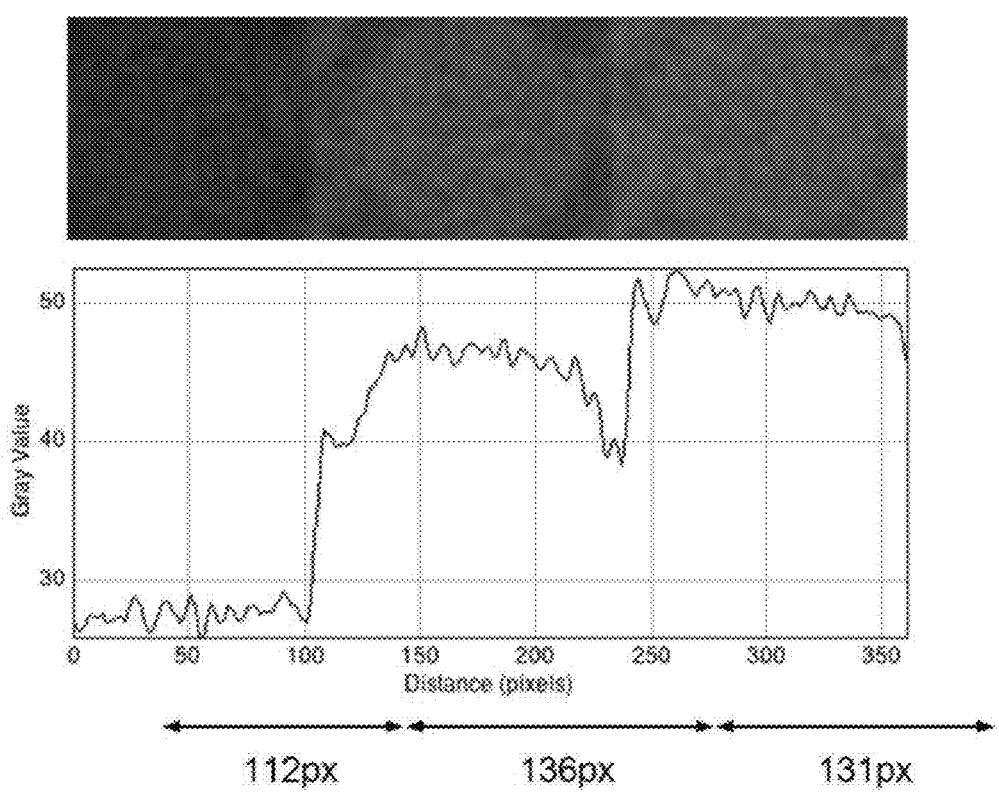

FIG. 38 illustrates an image depicting a profile step. The aluminum image plate width is 9.4 mm, total measured width in 379 pixels. Gray level on step wedge is 15/48/50.

Figure 39:
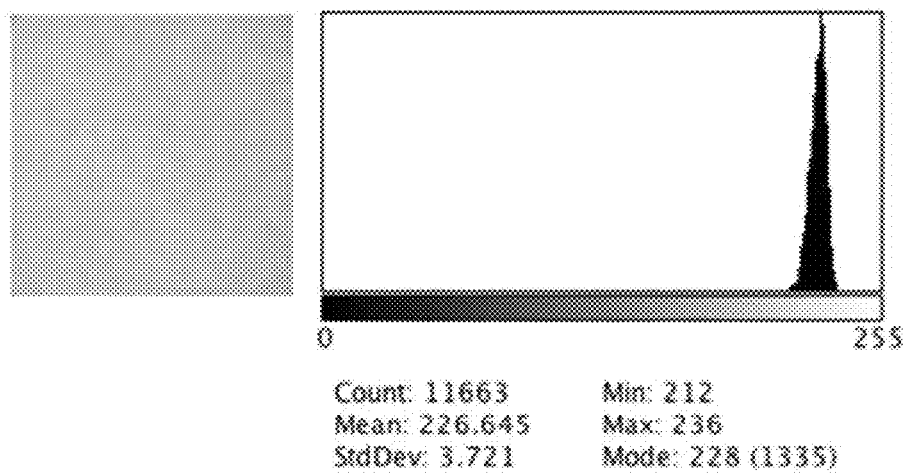
Figure 40:
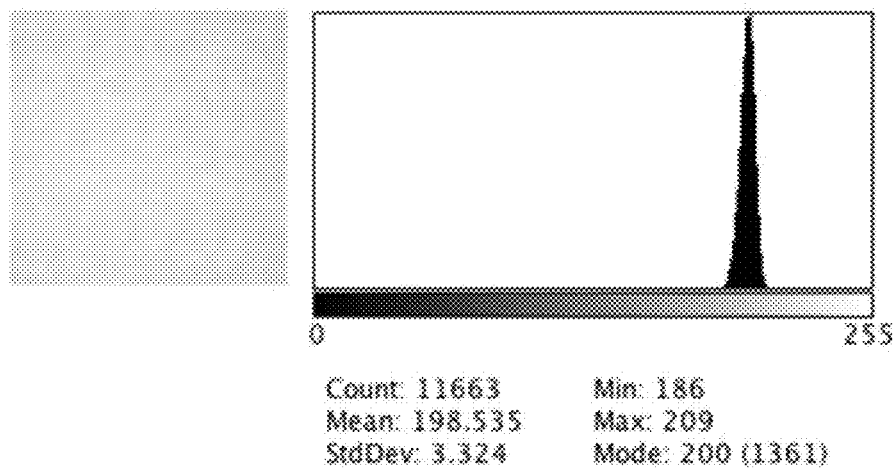

FIG. 39 illustrates a histogram of lead at the detector, and FIG. 40 illustrates a histogram of lead at entry.

FIG. 40 illustrates an image from a pediatric sensor with 0.3937 lp/mm mesh overlay profile long side.

Figure 41:
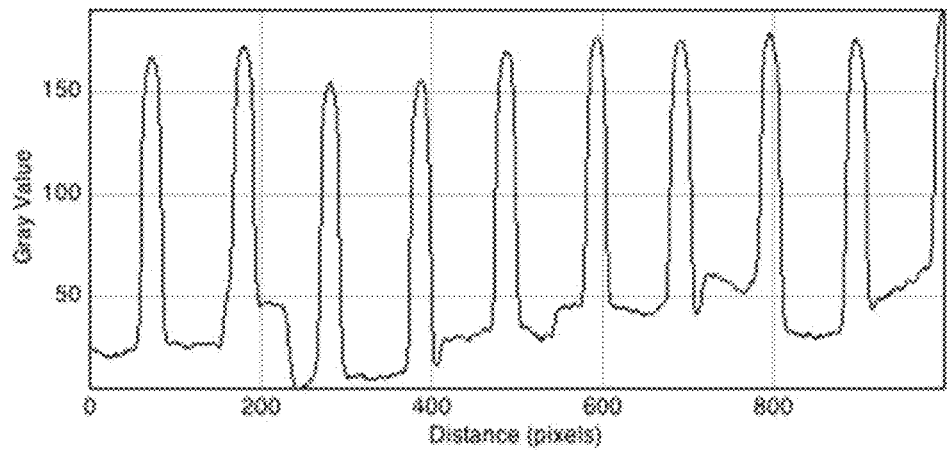
Figure 42:
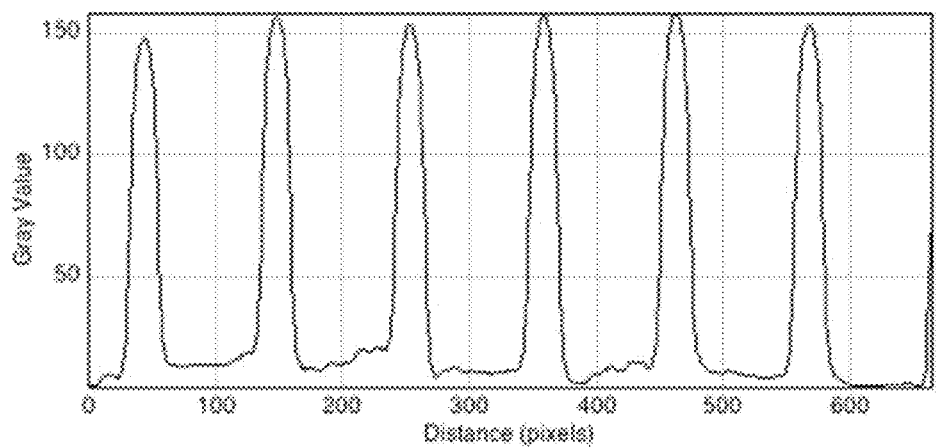

FIG. 41 illustrates a histogram of a pediatric sensor with 0.3937 lp/mm mesh overlay profile short side.

|        | G1     | G2    | G3    | G4      | G5      | G6     | G7     | R1     | R2     |
|--------|--------|-------|-------|---------|---------|--------|--------|--------|--------|
| Mean   | 13.096 | 4.867 | 0.203 | 198.867 | 227.165 | 40.970 | 50.322 | 80.062 | 66.776 |

Following calculation of comparison is based on contrast definition, where contrast=(a−b)/(a+b) formula is used.
Contrast scale: G3:G7=99.20%
Contrast between steps: G1:G2=45.81%; G1:G3=96.95%; G1:G7=58.70% G2:G3=91.99%; G2:G7=82.36%; G3/G7=99.20%
Tooth to background contrast: G6:G7=10.24%
lp/mm Limiting Resolution: R1 and R2 clearly visible
Scatter to primary ratio: (G5−G4)/(G7−G5)=16.00%

The scatter/primary ratio is indicative of the extent of off-focus radiation and of scatter originating between the focal spot and the entrance skin (i.e. from the filter and collimator).

Primary radiation comes straight from the focal spot, while scatter emanates from the other structures. This ratio is an indication of the age of the tube (off-focus radiation) and/or of poor design in the tube head and can be an indication of the performance of the x-ray unit.

Based on measurements made with the example phantom 720:

$$S/P=(D5-D4)/(D7-D5)$$

ie. since D5 is the effect of (Scatter+Base+Fog),
and D4 is the effect of (Base+Fog only),
Then (D5−D4) is the effect of Scatter only.
and since D7 is the effect of (Primary+Scatter+Base+Fog)
and D5 is the effect of (Scatter+Base+Fog),
Then (D7−D5) is the effect of Primary only.

Using the D values from the example dental test phantom 720 tests on four example units (#s 5, 12, 116 and 230), the S/P ratio ranges from 0.8 to 0.13.

The example dental test phantom 720 may be used to evaluate the contrast and the scatter-to-primary ratio in a typical exposure during a dental x-ray examination, to compare these data with what is considered an optimal exposure, and so to give the dentist guidance in optimizing the use of a given intraoral x-ray unit.

In the course of the examination of the example test units, the true kVp was measured using a digital kVp meter. The first HVT in aluminum was also evaluated. The mR exposure was measured using a dosimeter, and the FFD used in the practice was known.

A computer program (e.g., SR78) was used to calculate the intensity (in uGy/mAs) reaching the film under each of the irradiation conditions under the various absorbers in the phantom.

Ignoring for the moment the images of the mesh inserts used to determine resolution, we measure on each film (using a microdensitometer) the optical densities under each of the seven absorbers. The ideal operating criterion is to produce an OD of 1.5 under absorber 7 (the full 47.4 mm of PMMA). If this OD diverges from that value, we consider the exposure to be less than optimal.

So we create a table for each unit in which the OD's and the intensities are recorded. Since the OD=log Intensity, these values should be proportional.

Additional considerations on the design of a phantom for use in the examination of extraoral dental x-ray units. Given that digital receptors are now being used in intraoral dental imaging, this type of phantom is no longer necessary, since the receptor is already available.

The example dental test phantom 720 may be modified to match different detectors (e.g., 2.5 by 3.5 cm detector). In this case, the depth of the contrast holes or steps may be reduced to 6 mm, and the size of the five meshes may be reduced to 6 by 4 mm. This would leave room for a 6 mm diameter lead absorber and the tooth.

The use of film as the detector may require multiple exposures, film development, delayed receipt of information, and delayed transfer of the information to the computer and hence to the report. To eliminate these shortcomings, a digital phantom may be used and would exhibit the following advantages:

1 All the necessary data could be obtained with a single x-ray exposure. One or two repeat exposures could be made to confirm the results;
2. The data obtained from the multiple solid-state detectors could, after multiplexing, be passed via properly-designed software directly to the laptop in a form to match the layout of the report. The operator would see immediately after the exposure the data which would form the report.

A digital phantom would include a suitably-designed array of miniature radiation-sensitive diodes set into a PMMA block to function as sensors for providing the necessary data. The design of the array would incorporate the following:

1 Two centrally-placed entrance surface detectors, one to provide the dose/exposure and one (under a suitable attenuator) to provide a measurement of the kVp;
2. 8 detectors in a surface array to check on the beam alignment and dimension;
3. 8 detectors under increasing thicknesses of attenuator to measure contrast;
4. Resolution measurement using diffraction or interference.

Such a digital phantom would incorporate a multiplexer to pass the data from the detectors to the computer.

Example Calculations using the Example Dental Test Phantom 720:

Using measured 65 kVp: assume an 18 degree target; 2.2 mm Al total filtration (derived from measured HVT and Reilly's method).

Use the SR78 computer program to determine the Mean keV, the Air Kerma in μGy/mAs at 750 mm, and the 1st HVL.

Equivalency Calculations:

We are looking for a thickness of 1100 Al that is the equivalent of the 47.4 mm of PMMA in the phantom. Comparing the 47.4 mm thickness of PMMA to give the equivalent effects in mm Al.

| Added mm  | Mean keV | Air Kerma | 1st HVL | Notes on match      |
|-----------|----------|-----------|---------|---------------------|
| 47.4 PMMA | 40.5     | 24.7      | 3.07    | Standard to compare |
| 10.0 Al   | 45.6     | 14.7      | 4.83    |                     |
| 5.0 Al    | 42.6     | 35.5      | 3.56    |                     |
| 7.0 Al    | 44.0     | 24.2      | 4.3     |                     |
| 6.9 Al    | 43.9     | 24.7      | 4.26    | Best on Air Kerma   |
| 3.0 Al    | 40.9     | 55.9      | 3.2     | Best on keV, HVL    |

Result of calculations: It is apparent that there is no thickness that will give a reasonable match for all three parameters. 6.9 mm of Al gives the best match for intensity of radiation beyond the phantom, but the other two parameters are considerably different.

Dependency Calculations:

We now examine the effect of anode angle, using 47.4 PMMA absorber, and 65 kVp, 2.2 mm Al total filtration, at 750 mm.

| Anode angle | Mean keV | Air Kerma @ 750 mm | 1st HVL | Comments |
|---|---|---|---|---|
| 12 | 40.9 | 22.9 | 3.2 | |
| 18 | 40.5 | 24.9 | 3.07 | |
| 22 | 40.3 | 25.8 | 3.01 | |

Conclusion: It is apparent that the effect of anode angle is slight.

Calculations of Filtration Effect:

We next examine, at 65 KVP, the effect of total filtration, using 47.4 mm PMMA absorber, 18-degree anode angle, at 750 mm.

| Total Al Filter mm | Mean keV | Air Kerma | 1st HVL |
|---|---|---|---|
| 1.5 | 39.6 | 30.3 | 2.81 |
| 1.8 | 40.0 | 27.8 | 2.92 |
| 2.0 | 40.2 | 26.3 | 3.0 |
| 2.2 | 40.5 | 24.9 | 3.07 |
| 2.5 | 40.8 | 23.0 | 3.17 |

Conclusion: The effect of total filtration is surprisingly slight.

What is claimed is:

1. An imaging system for creating a bitewing image of a patient, the imaging system comprising:
   a transmitter;
   a detector; and
   a phantom assembly comprising
      at least one image plate made of at least one image plate material,
      at least one base member made of at least one base material, and
      a plurality of discrete surfaces formed on the base member; wherein
   the at least one base material is selected, sized, and dimensioned such that,
      when the phantom assembly is arranged in a test orientation along a transmission axis relative to the transmitter and the detector and exposed to x-rays,
      each of discrete surfaces is arranged at a different location along the transmission axis, and
      the phantom assembly simulates the attenuation and spectral response of x-ray exposures of patients;
   with the phantom assembly in the test orientation, the detector creates test data by detecting x-rays that propagate from the transmitter to the detector through the plurality of discrete surfaces formed on the base member and through the at least one image plate; and
   after the test data meets predetermined test criteria associated with attenuation and spectral response, a portion of the patient is arranged along the transmission axis between the transmitter and the detector such that the detector creates the bitewing image by detecting X-rays that propagate from transmitter to the detector through the portion of the patient.

2. An imaging system as recited in claim 1, in which:
   the phantom assembly further comprises at least one mesh insert, where the at least one mesh insert is selected, sized, and dimensioned such that, when the base member is exposed to x-rays, the at least one mesh insert allows measurement of resolution of the x-ray equipment; and
   the imaging system operates in the imaging configuration if the test data also meets predetermined test criteria associated with resolution.

3. An imaging system as recited in claim 1, further comprising a detector support system for supporting the detector in a desired orientation.

4. An imaging system as recited in claim 1, in which:
   the image plate material is metal; and
   the base material is plastic.

5. An imaging system as recited in claim 1, in which:
   the image plate material is aluminum; and
   the base material is acrylic.

6. An imaging system as recited in claim 1, in which:
   a plurality of recesses are formed in the base member to define the a plurality of discrete surfaces; and
   a transmitted energy test spectrum is associated with each step surface.

7. An imaging system as recited in claim 1, further comprising at least one image plate.

8. An imaging system as recited in claim 1, further comprising at least one lead plate.

9. An imaging system as recited in claim 1, further comprising a plurality of mesh inserts.

10. A method of calibrating an imaging system defining a transmission axis, the method comprising the steps of:
    providing a phantom assembly comprising
       at least one image plate made of at least one image plate material,
       at least one base member made of at least one base material, and
       a plurality of discrete surfaces formed on the base member, where
       the at least one base material is selected, sized, and dimensioned such that, when the phantom assembly is arranged in a test orientation along the transmission axis and exposed to x-rays,
          each of discrete surfaces is arranged at a different location along the transmission axis, and
          the phantom assembly simulates the attenuation and spectral response of x-ray exposures for bitewing images;
    with the phantom assembly in the test orientation, causing the imaging system to transmit x-rays along the transmission axis and through the plurality of discrete surfaces formed on the base member and through the at least one image plate to create test data; and
    determining whether the test data meets predetermined test criteria associated with attenuation and spectral response; and
    if the test data meets the predetermined test criteria associated with attenuation and spectral response,
       arranging a portion of the patient along the transmission axis, and
       causing the imaging system to transmit x-rays along the transmission axis and through the portion of the patient to create the bitewing image.

11. A method as recited in claim 10, in which:
    the step of providing the phantom assembly further comprises the step of supporting at least one mesh insert on the base member, where the at least one mesh insert is selected, sized, and dimensioned such that, when the base member is exposed to x-rays, the at least one mesh insert allows measurement of resolution of the x-ray equipment;

determining whether the test data meets predetermined test criteria associated with resolution; and operating the imaging system to create the bitewing image if the test data also meets the predetermined test criteria associated with resolution.

12. A method as recited in claim 10, further comprising the step of supporting the detector in a desired orientation relative to the phantom assembly.

13. A method as recited in claim 10, in which:
the image plate material is metal; and
the base material is plastic.

14. A method as recited in claim 10, in which:
the image plate material is aluminum; and
the base material is acrylic.

15. A method as recited in claim 10, in which:
a plurality of recesses are formed in the base member to define the a plurality of discrete surfaces; and
a transmitted energy test spectrum is associated with each step surface.

16. A method as recited in claim 10, further comprising at least one image plate.

17. A method as recited in claim 10, further comprising at least one lead plate.

18. A method as recited in claim 10, further comprising a plurality of mesh inserts.

19. An imaging system for creating a bitewing image of a patient, the imaging system that transmits x-rays along a transmission axis, comprising:
a phantom assembly comprising
at least one image plate made of at least one image plate material,
at least one base member made of at least one base material,
a plurality of discrete surfaces formed on the base member, and
at least one mesh insert; wherein
the at least one base material is selected, sized, and dimensioned such that,
when the phantom assembly is arranged in a test orientation relative to
the transmission axis and exposed to x-rays,
each of discrete surfaces is arranged at a different location along the transmission axis, and
the phantom assembly simulates the attenuation and spectral response of x-ray exposures for bitewing images;
the at least one mesh insert is selected, sized, and dimensioned such that, when the base member is exposed to x-rays, the at least one mesh insert allows measurement of resolution of the x-ray equipment;
with the phantom assembly in the test orientation, the imaging system creates test data by detecting x-rays that propagate along the transmission axis and through the plurality of discrete surfaces formed on the base member, through the at least one image plate, and through the at least one mesh member; and
after the test data meets predetermined test criteria associated with attenuation and spectral response and with resolution, a portion of the patient is arranged along the transmission axis such that the imaging system creates the bitewing image by detecting X-rays propagating through the portion of the patient.

20. An imaging system as recited in claim 19, in which:
the image plate material is aluminum; and
the base material is acrylic.

21. An imaging system as recited in claim 19, in which:
a plurality of recesses are formed in the base member to define the a plurality of discrete surfaces; and
a transmitted energy test spectrum is associated with each step surface.

* * * * *